US012144770B2

(12) United States Patent
Kebir et al.

(10) Patent No.: US 12,144,770 B2
(45) Date of Patent: Nov. 19, 2024

(54) SYSTEM AND METHOD FOR CONNECTING A PATIENT SUPPORT APPARATUS TO A HOSPITAL NETWORK

(71) Applicant: UMANO MEDICAL INC., L'Islet (CA)

(72) Inventors: Anouer Kebir, Saint-Jean-Chrysostome (CA); Steve Bolduc, Beaumont (CA); Esther Berthelot, Lévis (CA); Pascal Rousseau, Saint-Apollinaire (CA); Ahmed Atoubi, Saint-Nicolas (CA); Ghislain Demers, Beaumont (CA); Jérôme Marcotte, Lévis (CA)

(73) Assignee: UMANO MEDICAL INC., L'Islet (CA)

( * ) Notice: Subject to any disclaimer, the term of this patent is extended or adjusted under 35 U.S.C. 154(b) by 299 days.

(21) Appl. No.: 17/769,283

(22) PCT Filed: Oct. 16, 2020

(86) PCT No.: PCT/IB2020/059782
§ 371 (c)(1),
(2) Date: Apr. 14, 2022

(87) PCT Pub. No.: WO2021/074895
PCT Pub. Date: Apr. 22, 2021

(65) Prior Publication Data
US 2023/0329935 A1    Oct. 19, 2023

Related U.S. Application Data

(60) Provisional application No. 62/923,292, filed on Oct. 18, 2019.

(51) Int. Cl.
*A61G 7/05* (2006.01)
*A61B 5/00* (2006.01)
(Continued)

(52) U.S. Cl.
CPC ............ *A61G 7/0506* (2013.01); *G16H 20/40* (2018.01); *G16H 40/20* (2018.01); *G16H 40/63* (2018.01);
(Continued)

(58) Field of Classification Search
CPC ........ G16H 40/63; G16H 40/67; G16H 20/40; G16H 40/20; G16H 10/60; G16H 80/00;
(Continued)

(56) References Cited

U.S. PATENT DOCUMENTS

2004/0247023 A1   12/2004   Sasai et al.
2015/0082542 A1*   3/2015   Hayes ..................... H04W 4/02
                                                                455/456.1
(Continued)

FOREIGN PATENT DOCUMENTS

WO      2008/103177      8/2008

*Primary Examiner* — Justin C Mikowski
*Assistant Examiner* — Madison Emanski
(74) *Attorney, Agent, or Firm* — STEPTOE LLP; Scott Richey

(57) ABSTRACT

Methods and systems for connecting a patient support apparatus to a hospital network and locating the patient support apparatus are provided. A patient support apparatus is associated with a communication device having a first and second communication interface for transmitting and/or receiving a first and second type of wireless signal. The patient support apparatus is electrically connected to a node serving as a power output and a wireless communication system connected to the hospital network. In response to the electrical connection, the communication device activates the first communication interface to form a wireless link with the node. In response to the patient support apparatus being electrically disconnected from the node, the communication device activates the second communication inter-
(Continued)

face. The patient support apparatus is located by the node based on the second type of wireless signal.

27 Claims, 9 Drawing Sheets

(51) Int. Cl.
*A61B 5/11* (2006.01)
*A61G 7/018* (2006.01)
*G16H 20/40* (2018.01)
*G16H 40/20* (2018.01)
*G16H 40/63* (2018.01)
*G16H 40/67* (2018.01)

(52) U.S. Cl.
CPC .............. *G16H 40/67* (2018.01); *A61B 5/002* (2013.01); *A61B 5/1113* (2013.01); *A61G 7/018* (2013.01)

(58) Field of Classification Search
CPC .......... G16H 40/40; A61G 7/018; A61G 7/05; A61G 7/0506; A61G 7/012; A61G 7/015; A61G 2203/42; A61G 2205/60; H04W 4/80; H04W 4/02; H04W 4/30; H04W 64/00; H04W 12/50; A61B 5/1115; A61B 5/6891; A61B 5/002; A61B 5/1113; A61B 5/447; A61B 5/0002; A61B 5/6889; H04L 67/12; H04L 63/0853
USPC ............. 5/600, 430, 611; 340/539.1, 539.11, 340/573.1, 286.07, 539.12; 455/456.1; 34/539.11
See application file for complete search history.

(56) References Cited

U.S. PATENT DOCUMENTS

2017/0325091 A1 11/2017 Freeman et al.
2018/0344254 A1* 12/2018 George .................. G16H 40/63

* cited by examiner

SYSTEM AND METHOD FOR CONNECTING A PATIENT SUPPORT APPARATUS TO A HOSPITAL NETWORK

CROSS-REFERENCE

The present application is a national stage entry application under 35 U.S.C. § 371 of International Patent Application PCT/IB2020/059782, filed on Oct. 16, 2020, which claims the benefit of U.S. Provisional Patent Application Ser. No. 62/923,292 filed on Oct. 18, 2019. Each of these earlier application is incorporated herein by reference in its entirety.

FIELD

The present technology relates to a patient support apparatus in general and more specifically to system and method for connecting a patient support apparatus to a care facility network such as a hospital network.

BACKGROUND

Location detection systems are known in the art for tracking the location of personnel and equipment in facilities. These systems have been specifically adapted for use in facilities such as healthcare facilities for tracking healthcare professionals, e.g., nurses and physicians, and for tracking equipment, e.g., hospital beds, patient monitoring devices, and the like. Some location detection systems utilize tags that periodically transmit a unique identification signal. Receivers are located throughout the facility at known locations for receiving these identification signals. The receivers are wired to a central computer that processes the unique identification signals to determine a location of the asset associated with the tag.

Other location detection systems use transceivers positioned on board the patient support apparatuses and determine the locations of the patient support apparatuses based on signal strength data.

SUMMARY

It is an object of the present technology to ameliorate at least some of the inconveniences present in the prior art. One or more embodiments of the present technology may provide and/or broaden the scope of approaches to and/or methods of achieving the aims and objects of the present technology.

One or more embodiments of the present technology have been developed based on inventors' appreciation that in some instances, patient support apparatuses, such as hospital beds, may need to be located and tracked in a facility, such as a hospital for example. Due to various reasons, patient support apparatuses may be moved, may become inoperative, and may thus be difficult to track and locate.

Inventors of the present technology have appreciated that patient support apparatuses could be equipped with electronic devices for connecting the patient support apparatuses to a communication network, while using existing infrastructure and devices.

More specifically, inventors have appreciated that there is a need for a technology that could be convenient to use by a health professionals to automatically connect a patient support apparatus to a communication network, and where patient support apparatuses could be at least approximately located and/or tracked even if the patient support apparatuses are disconnected from the communication network.

One or more embodiments of the present technology enable connecting one or more patient support apparatuses to a communication network in a facility, such as a health care facility network, for instance a hospital network. A patient support apparatus is associated with an electronic device in the form of communication device having one or more communication interfaces which transmit and/or receive a first type of wireless signal and a second type of wireless signal. The first type of wireless signal and second type of wireless signal may be used to connect the one or more patient support apparatuses to a communication network and to locate the patient support apparatuses when they are disconnected from the communication network.

The present technology enables adapting existing patient support apparatuses with a simple and cost effective RLTS infrastructure. Among other features, the present technology may be used for locating beds with specific configurations, finding out which patient is in a bed as well as which bed a patient is located in.

Thus, embodiments of the present technology are directed to a system and a method for connecting a patient support apparatus to a hospital network.

In accordance with a broad aspect of the present technology, there is provided a method of connecting a patient support apparatus to a communication network. The patient support apparatus includes: a base, a patient support assembly mounted to the base, a patient support communication device includes: a processor, a first wireless communication interface operatively connected to the processor and is configured to be activated to transmit and receive a first type of wireless signal, and a second wireless communication interface operatively connected to the processor which is configured to be activated to transmit a second type of wireless signal. The patient support apparatus is electrically connectable to a power source, and the method is executed by the processor. The method comprises: receiving an indication of an electrical connection of the patient support apparatus to a wireless node to receive electrical power therefrom, the wireless node is electrically connected to a facility power source, the wireless node is connected to the communication network, in response to the receiving the indication of the electrical connection of the patient support apparatus to the wireless node: causing activation of the first wireless communication interface, receiving, from the wireless node, a first wireless signal, the first wireless signal is of the first type of wireless signal. In response to the receiving the first wireless signal: causing transmission of a second wireless signal of the first type, the transmitting thereby connecting the patient support apparatus to the wireless node, receiving an indication of the patient support apparatus being electrically disconnected from the wireless node, and in response to the receiving the indication of the electrical disconnection: causing activation of the second wireless communication interface.

In one or more embodiments of the method, the electrical connection is a wired electrical connection.

In one or more embodiments of the method, the processor is connected to a control unit of the patient support apparatus to receive the indication of the electrical connection and the electrical disconnection of the patient support apparatus.

In one or more embodiments of the method, causing activation of the second communication interface includes causing activation of the second communication interface in a discovery mode.

In one or more embodiments of the method, the receiving the indication of the electrical connection of the patient support apparatus includes receiving an indication of a unique password transmitted by the wireless node via the wired electrical connection, and the second wireless signal of the first type includes an indication of the unique password.

In one or more embodiments of the method, causing transmission of the second wireless signal includes causing transmission of an indication of a unique identifier of the patient support apparatus.

In one or more embodiments of the method, the causing the activation of the second communication interface includes causing transmission of a third wireless signal of the second type, the third wireless signal including an indication of a unique identifier of the patient support electronic device.

In one or more embodiments of the method, the second type of wireless signal has a shorter range than the first type of wireless signal.

In one or more embodiments of the method, the connecting the patient support apparatus to the wireless node is performed using a Wi-Fi® Protected Setup (WPS).

In one or more embodiments of the method, the second communication interface is at least one of: a Bluetooth® communication interface, and an ultra-wideband (UWB) communication interface.

In accordance with a broad aspect of the present technology, there is provided a patient support apparatus which includes a base, a patient support assembly connected to the base, and a patient support apparatus communication device mounted to one of the base and the patient support assembly. The patient support apparatus communication device includes: a processor, a first wireless communication interface operatively connected to the processor and is configured to be activated to transmit and receive a first type of wireless signal, and a second wireless communication interface operatively connected to the processor and is configured to be activated to transmit a second type of wireless signal. The patient support communication device is configured to: in response to the receiving an indication that the patient support apparatus is electrically connected to a wireless node, the wireless node is electrically connected to a facility power source: causing activation of the first wireless communication interface to connect the patient support apparatus communication device to the wireless node via the first type of wireless signal, and in response to the receiving an indication that the patient support apparatus is electrically disconnected from wireless node: causing activation of the second communication interface to transmit the second type of wireless signal.

In one or more embodiments of the patient support apparatus, the causing the activation of the second communication interface includes causing activation of the second communication interface into a discovery mode.

In one or more embodiments of the patient support apparatus, the second type of wireless signal has a shorter range than the first type of wireless signal.

In one or more embodiments of the patient support apparatus, the patient support electronic device is associated with a patient support apparatus identifier, and the patient support electronic device is configured to transmit an indication of the patient support apparatus identifier.

In accordance with a broad aspect of the present technology, there is provided a method for determining an approximate location of at least one patient support apparatus in a facility, the at least one patient support apparatus including a patient support apparatus communication device which includes at least one communication interface for transmitting a first type of wireless signal and a second type of wireless signal. The patient support apparatus communication device has been connected to a given one of a plurality of wireless nodes in the facility, and the method is executable by a processor connected to at least one of the plurality of wireless nodes over a communication network. The method includes: receiving, by the processor, previous wireless communication parameters associated with the at least one patient support apparatus, the previous wireless communication parameters having been determined by the given one of the plurality of wireless nodes by previously receiving the first of type of wireless signal from the patient support apparatus communication device of the at least one patient support apparatus. The method includes receiving, by the processor, current wireless communication parameters associated with the patient support apparatus communication device of the at least one patient support apparatus, the current wireless communication parameters having been determined by at least a portion of the plurality of wireless nodes by receiving the second type of wireless signal from the patient support apparatus communication device, comparing, by the processor, the previous wireless communication parameters and the current wireless communication parameters, and determining, by the processor, the approximate location of the at least one patient support apparatus based on the comparison of the previous wireless communication parameters and the current wireless communication parameters.

In one or more embodiments of the method, the at least one patient support apparatus has been previously electrically connected to the given one of the plurality of wireless nodes via an electrical wire to receive electrical power therefrom.

In one or more embodiments of the method, the at least one patient support apparatus has been previously connected to the given one of the plurality of wireless nodes via a wireless communication link.

In one or more embodiments of the method, the previous wireless communication parameters comprise: a unique identifier of at the least one patient support apparatus, and a previous inquiry response rate (IRR) of at the least one patient support apparatus.

In one or more embodiments of the method, the processor includes a processor of one of wireless nodes of the plurality of wireless nodes.

In one or more embodiments of the method, the processor includes a processor of the given wireless node.

In one or more embodiments of the method, the current wireless communication parameters are indicative of a current spatial density of patient support apparatuses in the facility.

In one or more embodiments of the method, the current wireless communication parameters are indicative of a past spatial density of patient support apparatuses in the facility.

In one or more embodiments of the method, the current wireless communication parameters comprise a current inquiry response rate (IRR) of the at least one patient support apparatus.

In one or more embodiments of the method, the previous wireless communication parameters includes a previous IRR of at least one patient support apparatus.

In one or more embodiments of the method, the determining the approximate location is performed by using a classification algorithm.

In one or more embodiments of the method, the determining the approximate location is performed by using a Kullback-Leibler (KL) divergence.

In one or more embodiments of the method, determining the approximate location is performed by using a Jensen Shannon (JS) divergence.

In accordance with a broad aspect of the present technology, there is provided wireless node includes: a power output interface connectable to a power source of a facility, a power input interface adapted to receive an electrical connection from a patient support apparatus, the power input interface is electrically connected to the power output interface, a processor operatively connected to the power output interface, a storage medium operatively connected to the processor, the storage medium includes computer-readable instructions, a first communication interface operatively connected to the processor, the first communication interface is operable to transmit and receive a first type of wireless signal to an electronic device, a second communication interface operatively connected to the processor, the second communication interface is operable to transmit and receive a second type of wireless signal to an electronic device. The processor, upon executing the computer-readable instructions, is configured to: receive a first wireless signal of the second type, determine, based on the first wireless signal of the second type, wireless communication parameters indicative of a presence of the patient support apparatus, in response to receiving an indication of an electrical connection of the patient support apparatus to the power input interface: receive a second wireless signal of the first type from the patient support apparatus, and transmit a third wireless signal of the first type to the patient support apparatus thereby forming a wireless communication link with the patient support apparatus.

In one or more embodiments of the wireless node, the wireless node further includes a third communication interface operatively connected to the processor, the third communication interface is connectable to a communication network.

In one or more embodiments of the wireless node, the processor is further configured to: in response to receiving an indication of the patient support apparatus is electrically disconnected from the power input interface: receive a fourth wireless signal of the second type, and determine, based on the fourth wireless signal of the second type, an approximate location of the patient support apparatus.

In one or more embodiments of the wireless node, the determining the approximate location is further based on the wireless communication parameters indicative of the presence of the patient support apparatus.

In one or more embodiments of the wireless node, the processor is further configured to, in response to receiving the indication of the electrical connection of the patient support apparatus to the power input interface: transmit, via the electrical connection of the patient support apparatus, a unique password, the processor is configured to transmit the third wireless signal of the first type in response to the second wireless signal of the first type includes the unique password.

In accordance with a broad aspect of the present technology, there is provided a method for connecting a patient support apparatus communication device associated with a patient support apparatus to nurse call system of a hospital, the method is executed by the patient support apparatus communication device, the patient support apparatus communication device includes a processor, a first communication interface operatively connected to the processor, the first communication interface for transmitting and receiving a first type of wireless signal, a second communication interface operatively connected to the processor, the second communication interface for transmitting a second type of wireless signal, the second type of wireless signal is different from the first type of wireless signal. The method includes: connecting, via the first communication interface, the patient support communication device to a communication network, transmitting, via the second communication interface, an indication of a presence of the patient support apparatus, receiving, via the first communication interface, an indication of a location of the patient support apparatus, the location having been determined based on the indication of the presence of the patient support apparatus having been received by a wireless node connected to the communication network, the wireless node having a wired connection to a nurse call system, and transmitting, via the first communication interface, a nurse call signal to the communication network, the nurse call signal thereby connecting the patient support apparatus communication device to the nurse call system of the hospital.

In one or more embodiments of the method, the wireless node is connected to the communication network via an Ethernet connection.

In one or more embodiments of the method, the first type of wireless signal includes an IEEE 802.11 standard signal.

In one or more embodiments of the method, the second type of wireless signal includes an ultrawide band (UWB) wireless signal.

In one or more embodiments of the method, the indication of the location of the patient support apparatus is received from a server connected to the communication network.

Implementations of the present technology each have at least one of the above-mentioned objects and/or aspects, but do not necessarily have all of them.

Additional and/or alternative features, aspects and advantages of implementations of the present technology will become apparent from the following description the accompanying drawings and the appended claims.

BRIEF DESCRIPTION OF THE DRAWINGS

For a better understanding of the present technology, as well as other aspects and further features thereof, reference is made to the following description which is to be used in conjunction with the accompanying drawings, where.

DETAILED DESCRIPTION

Figure 1:
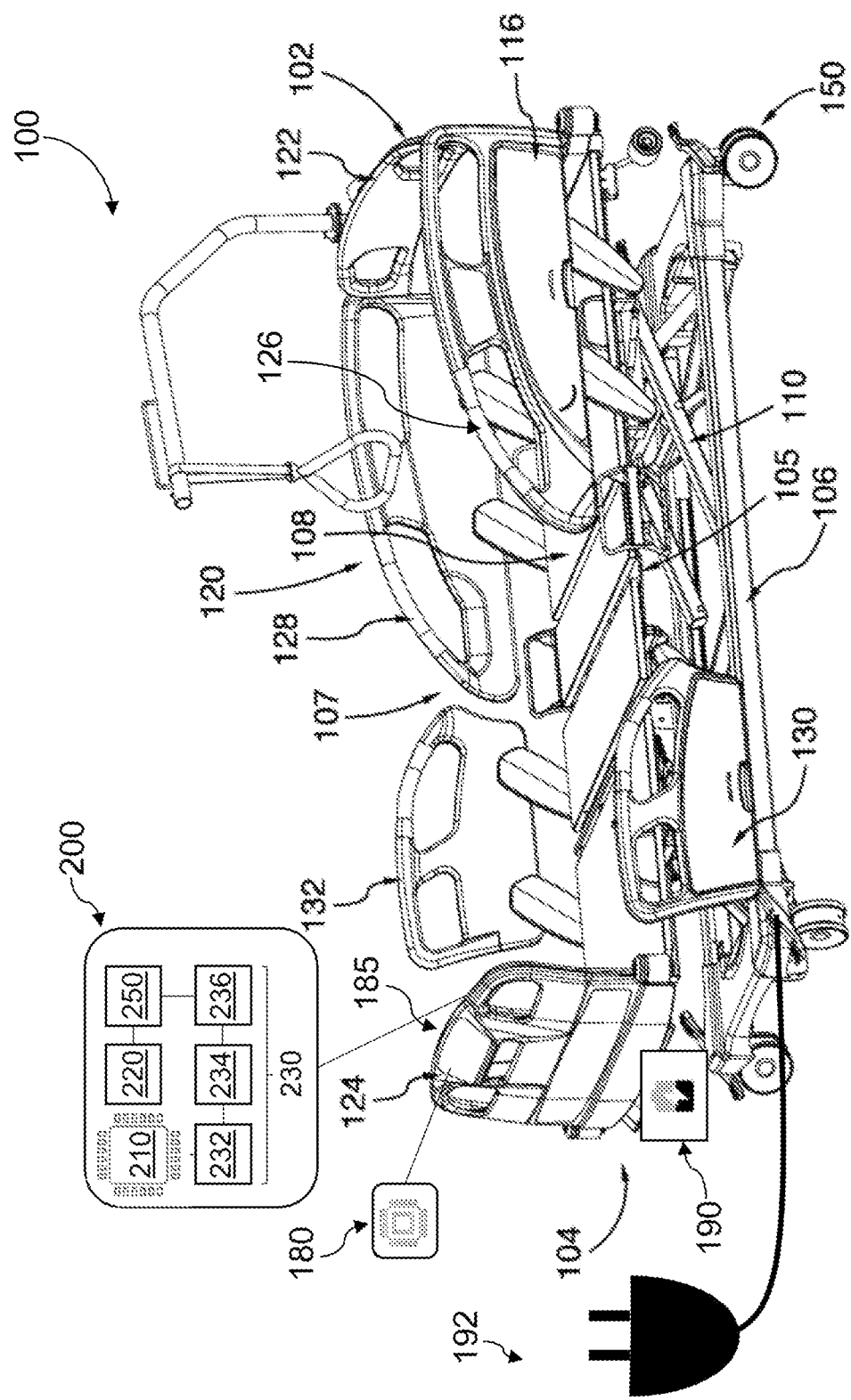
FIG. 1 depicts a schematic diagram of a patient support apparatus in accordance with non-limiting embodiments of the present technology.

The examples and conditional language recited herein are principally intended to aid the reader in understanding the principles of the present technology and not to limit its scope to such specifically recited examples and conditions. It will be appreciated that those skilled in the art may devise various arrangements which, although not explicitly described or shown herein, nonetheless embody the principles of the present technology and are included within its spirit and scope.

Definitions

In the context of the present specification, a "server" is a computer program that is running on appropriate hardware and is capable of receiving requests (e.g., from electronic devices) over a network (e.g., a communication network), and carrying out those requests, or causing those requests to be carried out. The hardware may be one physical computer or one physical computer system, but neither is required to be the case with respect to the present technology. In the present context, the use of the expression a "server" is not intended to mean that every task (e.g., received instructions or requests) or any particular task will have been received, carried out, or caused to be carried out, by the same server (i.e., the same software and/or hardware); it is intended to mean that any number of software elements or hardware devices may be involved in receiving/sending, carrying out or causing to be carried out any task or request, or the consequences of any task or request; and all of this software and hardware may be one server or multiple servers, both of which are included within the expressions "at least one server" and "a server".

In the context of the present specification, "electronic device" is any computing apparatus or computer hardware that is capable of running software appropriate to the relevant task at hand. Thus, some (non-limiting) examples of electronic devices include general purpose personal computers (desktops, laptops, netbooks, etc.), mobile computing devices, smartphones, and tablets, and network equipment such as routers, switches, and gateways. It should be noted that an electronic device in the present context is not precluded from acting as a server to other electronic devices. The use of the expression "an electronic device" does not preclude multiple electronic devices being used in receiving/sending, carrying out or causing to be carried out any task or request, or the consequences of any task or request, or steps of any method described herein. In the context of the present specification, a "client device" refers to any of a range of end-user client electronic devices, associated with a user, such as personal computers, tablets, smartphones, and the like.

In the context of the present specification, the expression "computer readable storage medium" (also referred to as "storage medium" and "storage") is intended to include non-transitory media of any nature and kind whatsoever, including without limitation RAM, ROM, disks (CD-ROMs, DVDs, floppy disks, hard drivers, etc.), USB keys, solid state-drives, tape drives, etc. A plurality of components may be combined to form the computer information storage media, including two or more media components of a same type and/or two or more media components of different types.

In the context of the present specification, a "database" is any structured collection of data, irrespective of its particular structure, the database management software, or the computer hardware on which the data is stored, implemented or otherwise rendered available for use. A database may reside on the same hardware as the process that stores or makes use of the information stored in the database or it may reside on separate hardware, such as a dedicated server or plurality of servers.

In the context of the present specification, the expression "information" includes information of any nature or kind whatsoever capable of being stored in a database. Thus, information includes, but is not limited to audiovisual works (images, movies, sound records, presentations etc.), data (location data, numerical data, etc.), text (opinions, comments, questions, messages, etc.), documents, spreadsheets, lists of words, etc.

In the context of the present specification, unless expressly provided otherwise, an "indication" of an information element may be the information element itself or a pointer, reference, link, or other indirect mechanism enabling the recipient of the indication to locate a network, memory, database, or other computer-readable medium location from which the information element may be retrieved. For example, an indication of a document could include the document itself (i.e. its contents), or it could be a unique document descriptor identifying a file with respect to a particular file system, or some other means of directing the recipient of the indication to a network location, memory address, database table, or other location where the file may be accessed. As one skilled in the art would recognize, the degree of precision required in such an indication depends on the extent of any prior understanding about the interpretation to be given to information being exchanged as between the sender and the recipient of the indication. For example, if it is understood prior to a communication between a sender and a recipient that an indication of an information element will take the form of a database key for an entry in a particular table of a predetermined database containing the information element, then the sending of the database key is all that is required to effectively convey the information element to the recipient, even though the information element itself was not transmitted as between the sender and the recipient of the indication.

In the context of the present specification, the expression "communication network" is intended to include a telecommunications network such as a computer network, the Internet, a telephone network, a Telex network, a TCP/IP data network (e.g., a WAN network, a LAN network, etc.), and the like. The term "communication network" includes a wired network or direct-wired connection, and wireless media such as acoustic, radio frequency (RF), infrared and other wireless media, as well as combinations of any of the above.

In the context of the present specification, the words "first", "second", "third", etc. have been used as adjectives only for the purpose of allowing for distinction between the nouns that they modify from one another, and not for the purpose of describing any particular relationship between those nouns. Thus, for example, it should be understood that, the use of the terms "first server" and "third server" is not intended to imply any particular order, type, chronology, hierarchy or ranking (for example) of/between the server, nor is their use (by itself) intended to imply that any "second server" must necessarily exist in any given situation. Further, as discussed herein in other contexts, reference to a "first" element and a "second" element does not preclude the two elements from being the same actual real-world element. Thus, for example, in some instances, a "first" server and a "second" server may be the same software and/or hardware, in other cases they may be different software and/or hardware.

Furthermore, as an aid to understanding, the following description may describe relatively simplified implementations of the present technology. As persons skilled in the art would understand, various implementations of the present technology may be of a greater complexity.

In some cases, what are believed to be helpful examples of modifications to the present technology may also be set forth. This is done merely as an aid to understanding, and, again, not to define the scope or set forth the bounds of the present technology. These modifications are not an exhaustive list, and a person skilled in the art may make other modifications while nonetheless remaining within the scope of the present technology. Further, where no examples of modifications have been set forth, it should not be interpreted that no modifications are possible and/or that what is described is the sole manner of implementing that element of the present technology.

Moreover, all statements herein reciting principles, aspects, and implementations of the present technology, as well as specific examples thereof, are intended to encompass both structural and functional equivalents thereof, whether they are currently known or developed in the future. Thus, for example, it will be appreciated by those skilled in the art that any block diagrams herein represent conceptual views of illustrative circuitry embodying the principles of the present technology. Similarly, it will be appreciated that any flowcharts, flow diagrams, state transition diagrams, pseudocode, and the like represent various processes which may be substantially represented in computer-readable media and so executed by a computer or processor, whether or not such computer or processor is explicitly shown.

The functions of the various elements shown in the figures, including any functional block labeled as a "processor" or a "graphics processing unit", may be provided through the use of dedicated hardware as well as hardware capable of executing software in association with appropriate software. When provided by a processor, the functions may be provided by a single dedicated processor, by a single shared processor, or by a plurality of individual processors, some of which may be shared. In some non-limiting embodiments of the present technology, the processor may be a general purpose processor, such as a central processing unit (CPU) or a processor dedicated to a specific purpose, such as a graphics processing unit (GPU). Moreover, explicit use of the term "processor" or "controller" should not be construed to refer exclusively to hardware capable of executing software, and may implicitly include, without limitation, digital signal processor (DSP) hardware, network processor, application specific integrated circuit (ASIC), field programmable gate array (FPGA), read-only memory (ROM) for storing software, random access memory (RANI), and non-volatile storage. Other hardware, conventional and/or custom, may also be included.

Software modules, or simply modules which are implied to be software, may be represented herein as any combination of flowchart elements or other elements indicating performance of process steps and/or textual description. Such modules may be executed by hardware that is expressly or implicitly shown.

With these fundamentals in place, we will now consider some non-limiting examples to illustrate various implementations of aspects of the present technology.

Hospital Bed

Referring first to FIG. 1, there is shown a patient support apparatus, in this case a hospital bed 100, in accordance with one embodiment of the present technology. The hospital bed 100 comprises a head end 102, an opposite foot end 104 and spaced-apart left 105 and right 107 sides extending between the head end 102 and the foot end 104.

Some of the structural components of the hospital bed 100 will be designated hereinafter as "right", "left", "head" and "foot" from the reference point of an individual lying on his/her back on the support surface of the mattress provided on the hospital bed 100 with his/her head oriented toward the head end 102 of the hospital bed 100 and the his/her feet oriented toward the foot end 104 of the hospital bed 100.

The hospital bed 100 includes a base 106, a patient support assembly 108 and an elevation system 110 operatively coupling the patient support assembly 108 to the base 106. In the illustrated embodiment, the patient support assembly 108 includes a frame (not numbered) and a patient support surface (not numbered) supported by the frame. In the illustrated embodiment, the patient support surface (not numbered) includes an upper body surface or backrest (not numbered), a lower body surface or lower body support panel (not numbered) and one or more core body surfaces or core support panels (not numbered) located between the backrest (not numbered) and the lower body support panel (not numbered) for supporting the seat and/or thighs of the patient. In the illustrated embodiment, each one of the backrest (not numbered), the lower body support panel (not numbered) and the core support panels (not numbered) can be angled relative to the other panels. Alternatively, the patient support surface (not numbered) could comprise a single rigid panel extending between the head end 102 and the foot end 104 of the hospital bed 100 instead of multiple pivotable panels.

The hospital bed 100 further includes a patient support barrier system 120 generally disposed around the patient support assembly 108. The barrier system 120 includes a plurality of barriers which extend generally vertically around the patient support assembly 108. In the illustrated embodiment, the plurality of barriers includes a headboard 122 located at the head end 102 and a footboard 124 disposed generally parallel to the headboard 122 and located at the foot end 104 of the hospital bed 100. The plurality of barriers further include spaced-apart left and right head siderails 126, 128 which are located adjacent the headboard 122 and spaced-apart left and right foot siderails 130, 132 which are respectively located between the left and right head siderails 126, 128 and the foot end 104 of the hospital bed 100. Each one of the siderails 126, 128, 130 and 132 is moveable between an extended or raised position for preventing the patient lying on the hospital bed 100 from moving laterally out of the hospital bed 100, and a retracted or lowered position for allowing the patient to move or be moved laterally out of the hospital bed 100.

The hospital bed 100 further includes a plurality of pivoting systems including one or more actuators for pivoting one or more of the backrest (not numbered), the lower body support panel (not numbered) and the core support panels (not numbered) relative to the frame (not numbered). The hospital bed 100 may further include a plurality of sensors for sensing different parameters of the hospital bed 100, such as bed configuration (e.g. angles and positions of the backrest, lower body and core support panels, height of the elevation system, etc.), or for sensing parameters related to the patient (patient weight, location of the patient, etc.).

The hospital bed 100 includes a control unit 180 or controller 180 operatively connected to inter alia the elevation system 110, the plurality of pivoting systems (not numbered) and the plurality of sensors (not shown) for receiving and transmitting signals thereto. The control unit 180 may be operatively connected to the components of the hospital bed 100 via a circuitry (not shown). The control unit 180 is used to control various functions of the hospital bed 100. In one embodiment, the control unit 180 is mounted on the patient support assembly 108, for example below one of the panels of the patient support surface.

The hospital bed 100 may further include a control interface (or input/output interface) 185 operatively connected to the control unit 180. The control interface 185 could be integrated into the footboard 124, into the headboard 122 or into one or more of the siderails 126, 128, 130, 132. Alternatively, the control interface 185 could be provided as a separate unit located near the hospital bed 100 or even at a location remote from the hospital bed 100 and operatively connected to the hospital bed 100. The control interface 185 is operatively connected to the control unit 180 from which it receives and transmits signals, such as signals from sensor(s), actuators and other mechanisms on the hospital bed 100. The control interface 185 may for example display sensed parameters and configuration parameters and allow a user to transmit commands to the control unit for controlling various functions of the hospital bed 100, such as actuating the actuators for pivoting panels, controlling the elevation system 110, and the like. As a non-limiting example, the control interface 185 may be implemented as a touchscreen, as a digital screen with physical input buttons or touch pads, or a combination thereof.

The hospital bed 100 further includes a portable power source 190, such as battery, to which the circuitry and the control unit 180 of the hospital bed 100 is electrically connected and receives power from.

The hospital bed 100 is also electrically connectable to a permanent power source of a facility, such as an electrical grid of a hospital. The hospital bed 100 is electrically connectable to the permanent power source via an electrical connection wire 192. Generally speaking, when electrically connected to the permanent power source via the electrical connection wire 192, the hospital bed 100 does not receive electrical power from the portable power source 190 and/or provide power to recharge portable power source 190. In one embodiment, the electrical connection wire 192 can be configured to transmit data between an electronic circuitry of the hospital bed 100 and a wireless node (which will be explained in more detail herein below). In one embodiment, power-line communication (PLC) may be used to transmit data over the electrical connection wire 192.

Hospital Bed Communication Device

In one embodiment, the hospital bed 100 further comprises a hospital bed communication device 200. In some embodiments, the hospital bed communication device 200 is operatively connected to inter alia the control unit 180 of the hospital bed 100, as will be described in more detail herein below. In other embodiments, the hospital bed communication device 200 may be a separate electronic device added to the hospital bed 100, and may be communicatively connected to the control unit 180 via a dedicated wired or wireless communication interface (not shown). In alternative embodiments, the hospital bed communication device 200 is not connected to the control unit 180 of the hospital bed 100. As it will become apparent below, the hospital bed communication device 200 allows communication with an electronic device (e.g. a wireless node 400 depicted in FIG. 2 and/or portable electronic devices, as detailed below) and/or a communication network (e.g. a hospital communication network 460 depicted in FIG. 3).

The hospital bed communication device 200 is configured to inter alia: (i) store parameters related to the hospital bed 100 and/or the hospital bed communication device 200 (ii) transmit and/or receive a first type of wireless signal for establishing a communication link and connecting the hospital bed 100 to one or more networks; (iii) transmit and/or receive a second type of wireless signal which enable locating the hospital bed 100 in an environment such as in a hospital room or hallway.

How the hospital bed communication device 200 is configured to do so will be explained in more detail herein below.

In some embodiments, the hospital bed communication device 200 is physically separate or distinct from the components of the hospital bed 100 (e.g. a retrofittable or portable hospitable bed communication devices 200). In this embodiment, the hospital bed communication device 200 can be positioned adjacent to the hospital bed 100 and may be mounted on one or more of the components of the hospital bed 100 such as the base 106, the patient support assembly 108, or to the patient support barrier system 120.

In other embodiments, the hospital bed communication device 200 may be integrated into the hospital bed 100. For instance, the hospital bed communication device 200 could be integrated into the footboard 124, into the headboard 122, into one or more of the siderails 126, 128, 130, 132 or into a control box (not shown) embedding the control unit 180 and mounted to the patient support assembly 108.

The hospital bed communication device 200 comprises inter alia a processor 210, a storage medium 220, a set of communication interfaces 230 including a first wireless communication interface 232, a second communication interface 234, a third communication interface 236, and an input/output interface 250, operatively connected to each other. The hospital bed communication device 200 may comprise an independent power source such as battery (not shown) or it may be connected to a power source of the hospital bed 100, such as the portable power source 190 or the electrical connection wire 192.

It will be appreciated that the nature of the connection between the processor 210, the storage medium 220, and the set of communication interfaces 230 is not limited and depends on how the hospital bed communication device 200 is implemented. In one or more embodiments, one or more of the processor 210, the storage medium 220, the set of communication interfaces 230 and the input/output interface 250 may be part of an integrated circuit (IC) or may be connected using internal and/or external buses (e.g. a PCI bus, universal serial bus, IEEE 1394 "Firewire" bus, SCSI bus, Serial-ATA bus, etc.).

The hospital bed communication device 200 may store in the storage medium data related to the hospital bed 100, the hospital bed communication device 200, the patient of the hospital bed 100 and its environment. In one embodiment, the hospital bed communication device 200 stores one or more of a hospital bed identifier, a communication device identifier, configuration parameters of the hospital bed 100 (which may be transmitted by the control unit 180 of the hospital bed), patient data, location data, unique passwords and the like. Non-limiting examples of communication device identifiers include a MAC address, a World Wide Port name, and a universally unique identifier (UUID).

The hospital bed communication device 200 may transmit data stored in the storage medium via the set of communication interfaces 230, as it will become apparent below.

The input/output interface 250 may comprise connections ports for connecting other components or other electronic devices (e.g. a computer for configuring the hospital bed communication device 200, or a portable device of healthcare worker) to the hospital bed communication device 200 for configuration thereof. In some embodiments, the input/output interface 250 comprises a display screen (e.g. a LCD screen or touchscreen) and an input device (e.g. touchscreen, keypad, etc).

In some embodiments, the hospital bed communication device 200 is connected via a wired or wireless communication link to the control unit 180 and control interface 185 of the hospital bed 100, which may enable the hospital bed communication device 200 to receive parameters of the hospital bed 100 and/or transmit command signals received from other electronic devices connected to the set of communication interfaces 230 of the hospital bed 100. In such embodiments, the hospital bed communication device 200 may not necessarily have the processor 210 and the storage medium 220, and at least a portion of the functionalities of the processor 210 and/or the storage medium may be provided by the control unit 180. The hospital bed communication device 200 may thus enable external electronic devices (e.g. computers, smartphones and the like) having communication interfaces to receive and/or transmit information to the control unit 180 of the hospital bed 100. In some embodiments, the hospital bed communication device 200 may receive and/or transmit information to other hospital bed communication devices (not shown) associated with respective hospital beds (not shown) as well as other medical devices having adapted communication interfaces.

In some embodiments, the hospital bed communication device 200 further comprises a first power interface (not shown) connected to the portable power source 190 of the hospital bed 100, and a second power interface (not shown) connected to the electrical connection wire 192. The second power interface (not shown) may be directly connected to the electrical connection wire 192 or may be connected to other electrical components of the hospital bed 100 which connect to the electrical connection wire 192. The second power interface (not shown) enables receiving electrical power and/or data via the electrical connection wire 192. In one embodiment, the hospital bed communication device 200 implements power-line communication (PLC) components to receive and/or transmit data via the electrical connection wire 192. In one embodiment, the hospital bed communication device 200 implements universal asynchronous receiver-transmitter (UART) components for serial communication via the electrical connection wire 192. Thus, in such embodiments, the hospital bed communication device 200 may receive and/or transmit data via the electrical connection wire 192. In alternative embodiments, the hospital bed communication device 200 comprises power over Ethernet (PoE) components (e.g., with the third communication interface 236) for receiving and transmitting data and electrical power via communication links.

As a non-limiting example, the hospital bed communication device 200 can be implemented as a Bluetooth® and WiFi® integrated microcontroller. As another non-limiting example, the hospital bed communication device 200 can be implemented as an ultrawide band (UWB) and WiFi® integrated microcontroller. As yet another non-limiting example, the hospital bed communication device 200 can be implemented as a UWB, Bluetooth® and WiFi® integrated microcontroller.

In some embodiments, the hospital bed communication device 200 may be implemented as an embedded system including a microcontroller, a system on a chip (SoC) and the like. In other embodiments, the hospital bed communication device 200 may be implemented as a computer, a smartphone, a tablet, and the like.

Hospital Bed First Communication Interface

Figure 2:
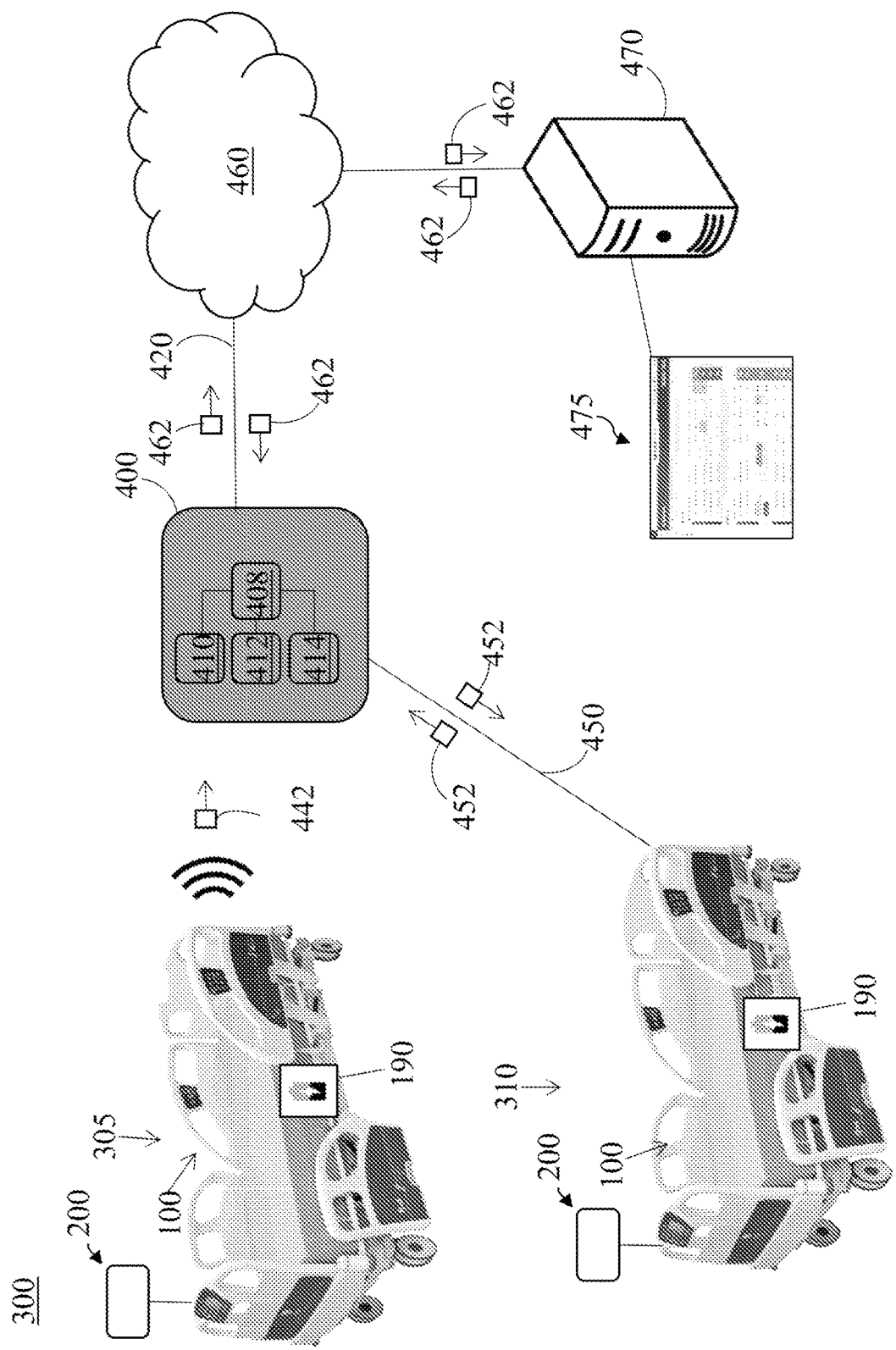
FIG. 2 depicts a schematic diagram of a first hospital bed communication system in accordance with non-limiting embodiments of the present technology.
Figure 3:
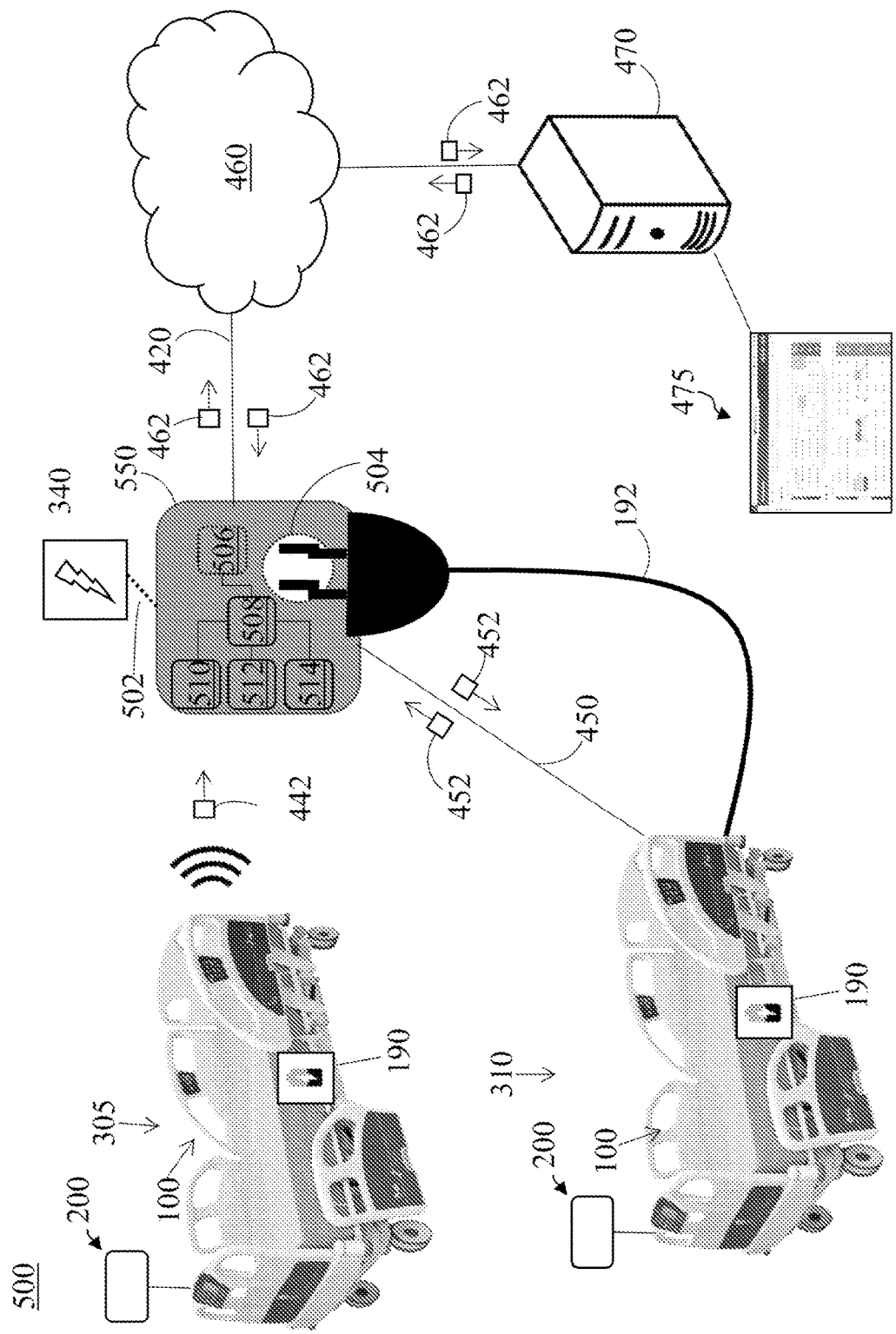
FIG. 3 depicts a schematic diagram of a second hospital bed communication system with wireless node comprising power input and output interfaces in accordance with non-limiting embodiments of the present technology.

The first wireless communication interface 232 is configured to transmit and/or receive a first type of wireless signal for connecting the hospital bed communication device 200 to one or more electronic devices having adapted communication interfaces (such as the wireless node 400 and the central computer 470 depicted in FIG. 2), and/or to a communication network (such as the hospital communication network 460 depicted in FIG. 3).

In one embodiment, by transmitting and receiving the first type of wireless signal, a wireless communication link (e.g. first wireless communication link 450 in FIG. 3) may be established between the hospital bed communication device 200 and other electronic devices having adapted communication interfaces similar to the first wireless communication interface 232, which may enable exchange of information therebetween.

In one embodiment, the first wireless communication interface 232 enables communication based on the Institute of Electrical and Electronics Engineers (IEEE) 802.11 standard, the implementation of which is known in the art. In one embodiment, the first wireless communication interface 232 implements a TCP/IP and full 802.11 b/g/n Wi-Fi® MAC protocol, supports the Basic Service Set (BSS) STA and SoftAP operations under the Distributed Control Function (DCF), and power management may be handled with minimal host interaction to minimize the active-duty period. In another embodiment, the first wireless communication interface 232 may enable to transmit IEEE 802.15.4 ultra-wideband (UWB) signals.

Hospital Bed Second Communication Interface

The second wireless communication interface 234 is configured to transmit and/or receive a second type of wireless signal. The second type of wireless signal transmitted by the second wireless communication interface 234 is used for locating at least approximately the hospital bed communication device 200 associated with the hospital bed 100.

In some embodiments, the second wireless communication interface 234 is a RF transmission module comprising an RF antenna. In one embodiment, the second wireless communication interface 234 enables transmission of the second type of wireless signal in a range varying from about 0.5 m to about 100 m. It should be understood that the nature of the second type of wireless signal is not limited, and the second type of wireless signal is a wireless signal having a shorter range than the first type of wireless signal, and does not preclude the second wireless communication interface 234 from transmitting different "subtypes" of second wireless signals.

In some embodiments, the second wireless communication interface 234 is configured to transmit the second type of wireless signal in the form of beacons, i.e. signals indicative of a proximity or location of the hospital bed communication device 200. It will be appreciated that the second type of wireless signal may also carry indications of constant and changing parameters relative to the hospital bed communication device 200 and/or to the hospital bed 100, such as power-supply information, relative address, location, timestamp, signal strength, available bandwidth resources, temperature, pressure and the like.

In the context of the present technology, the second wireless communication interface 234 may be part of a real-time location system (RLTS) and the second type of wireless signal may be used to approximate a location of the hospital bed 100. In some embodiments, the second wireless communication interface 234 comprises only a transmitter. In other embodiments, the second wireless communication interface 234 comprises one or more transmitters and one or more receivers (or transceivers). In alternative embodiments, the second wireless communication interface 234 may provide the functionality of an active tag, a passive tag or a combination thereof.

In one embodiment, the second wireless communication interface 234 is configured in a master/slave architecture. In one embodiment, the second wireless communication interface 234 comprises a Bluetooth® communication module. In one embodiment, the second wireless communication interface 234 comprises a Bluetooth® link controller (not shown) and a Bluetooth® baseband (not shown), complies with the Bluetooth® 4.2+ enhanced data rate (EDR) specification, and implements the baseband protocols and other low-level link routines, such as modulation/demodulation, packet processing, bit stream processing, frequency hopping, and the like. In one embodiment, the second wireless communication interface 234 operates in a standby state, a connection state, and a sniff state and enables multiple connections, and other operations, such as inquiry, page, and secure simple-pairing, Piconet and Scat-ternet.

In one embodiment, the second wireless communication interface 234 comprises a Bluetooth® Low Energy (BLE) communication module. Additionally or alternatively, the second wireless communication interface 234 comprises an ultra-wideband (UWB) communication module which transmits IEEE 802.15.4 ultra-wideband signals.

In some embodiments, the second wireless communication interface 234 may be configured to beacon a unique identifier at predetermined intervals. In other embodiments, the second wireless communication interface 234 may be configured to transmit the unique identifier upon receiving an indication to do so.

In one embodiment, the second wireless communication interface 234 transmits the second type of wireless signal by using frequency-hopping spread-spectrum.

In some embodiments, the hospital bed communication device 200 is configured to selectively switch the second wireless communication interface 234 into a "discovery" mode. The discovery mode enables an electronic device having a communication interface adapted to receive the second type of wireless signal to receive the second type of wireless signal transmitted by the hospital bed communication device 200 without establishing a communication link. The purpose of the discovery mode is for the hospital bed communication device 200 to broadcast its presence to other electronic devices within range of the second type of wireless signal.

It should be noted that in the context of the present technology, the second wireless communication interface 234 does not need to establish a communication link with any of the devices while in the discovery mode, i.e. while other electronic devices may receive and/or transmit data packets to the hospital bed communication device 200, a permanent communication link does not need to be established between the hospital bed communication device 200 and other electronic devices (e.g. computers, smartphones, other hospital bed communication devices, communication interfaces of medical devices, wireless access points and the like). In alternative embodiments, the second wireless communication interface 234 may be configured to establish a wireless communication link.

Hospital Bed Third Communication Interface

In one embodiment, the hospital bed communication device 200 has a third communication interface 236. The third communication interface 236 provides a two-way data communication coupling to a communication link (not shown) to exchange information. In one or more embodiments, the third communication interface 236 enables coupling the patient device with a wired connection to a communication network. As a non-limiting example, the third communication interface 274 may be an integrated services digital network (ISDN) card, cable modem, satellite modem, or a modem to provide a data communication connection to a corresponding type of telephone line. As another non-limiting example, the third communication interface 236 may be used to connect to a local area network (LAN) card to provide data communication to a LAN via a wired communication link such as Ethernet. In any such implementation, the third communication interface 236 may be configured to sends and receives electrical, electromagnetic or optical signals that carry digital data streams representing various types of information. Additionally or alternatively, the third communication interface 236 may provide an interface for connection to a nurse call system of the hospital.

In some embodiments, the hospital bed communication device 200 is configured to monitor and selectively activate and deactivate each of the first wireless communication interface 232, the second wireless communication interface 234, and the third communication interface 236.

The hospital bed communication device 200 is configured to activate the second wireless communication interface 234 to transmit the second type of wireless signal for enabling localization of the hospital bed 100 in response to or upon receiving an indication to do so. The indication may be received from the set of communication interfaces 230 such as the second wireless communication interface 234, via an input/output interface of the hospital bed communication device 200, or via the control unit 180 of the hospital bed 100.

In some embodiments, the processor 210 of the hospital bed communication device 200 may monitor a connection status of the first wireless communication interface 232 and/or the third communication interface 236, which may transmit an indication that there is no communication link established via the first wireless communication interface 232 and/or the third communication interface 236, and the hospital bed communication device 200 may cause activation of the second wireless communication interface 234 in response thereto.

In some embodiments, the indication causing the hospital bed communication device 200 to activate the second wireless communication interface 234 may be transmitted from the control unit 180 of the hospital bed 100, via for example the control interface 185. In other embodiments, the indication may comprise an indication that the hospital bed 100 is electrically disconnected from a power source e.g., the electrical connection wire 192 is disconnected from a power outlet of the hospital, which may be received from the control unit 180 or a circuit of the hospital bed 100.

In some embodiments, the hospital bed communication device 200 may activate the second wireless communication interface 234 in a "discovery" mode. In other embodiments, the second wireless communication interface 234 may always be active to transmit the second type of wireless signal.

The hospital bed communication device 200 is configured to activate the first wireless communication interface 232 to transmit and receive the first type of wireless signal for establishing a communication link and exchanging data to connected electronic devices in response to or upon receiving an indication to do so. The first communication interface 232 may connect the hospital bed communication device 200 directly to a communication network (e.g., the Internet, a LAN, a LTE network and the like) or to an electronic device having adapted communication interfaces for receiving and transmitting the first type of wireless signal.

In some embodiments, the indication causing the hospital bed communication device 200 to activate the first wireless communication interface 232 may be transmitted from the control unit 180 of the hospital bed 100, via for example the control interface 185. Additionally or alternatively, the indication may comprise an indication that the hospital bed 100 is electrically connected to a power source e.g., the electrical connection wire 192 is connected to a power outlet of the hospital.

In some embodiments, the hospital bed communication device 200 is configured to deactivate at least partially the second wireless communication interface 234 to stop transmission of the second type of wireless signal for enabling localization of the hospital bed 100 when the first communication interface 232 is active and a communication link has been established.

First System

With reference to FIG. 2, there is depicted a schematic diagram of a first hospital bed communication system 300 in accordance with one or more embodiments of the present technology.

The first hospital bed communication system 300 or system 300 comprises inter alia the hospital bed 100 and the associated hospital bed communication device 200, a wireless node 400, and a hospital communication network 460.

In FIG. 2, the hospital bed 100 and the associated hospital bed communication device 200 are depicted in two states: a disconnected state 305 and a connected state 310.

In the disconnected state 305, the hospital bed communication device 200 has not established the first wireless communication link 450 via the first wireless communication interface 232. In this disconnected state 305, the hospital bed communication device 200 is configured to activate the second wireless communication interface 234 to transmit the second type of wireless signal for enabling localization of the hospital bed 100 in the form of data packets 442. As stated previously, the hospital bed communication device 200 may activate the second wireless communication interface 234 in a "discovery" mode. In some embodiments, in the disconnected state 305, the hospital bed communication device 200 is configured to deactivate the first wireless communication interface 232.

In the connected state 310, the hospital bed communication device 200 has established a first wireless communication link 450 via the first wireless communication interface 232. The first wireless communication link 450 enables the hospital bed communication device 200 to transmit and receive data packets 452. In some embodiments, when in the connected state 310, the hospital bed communication device 200 is configured to deactivate at least partially the second wireless communication interface 234 to stop transmission of the second type of wireless signal for enabling localization of the hospital bed 100.

In FIG. 2, the hospital bed communication device 200 in the connected state 310 has established this first wireless communication link 450 with the wireless node 400, which will now be described.

Wireless Node

Still referring to FIG. 2, the wireless node 400, also referred to as wireless access point 400, comprises inter alia a microcontroller 408, a first communication interface 410, a second communication interface 412, and a third communication interface 414.

The wireless node 400 is configured to inter alia: (i) connect, via the third communication interface 414, to the hospital communication network 460; (ii) transmit and receive first type of wireless signal to connect, via the first communication interface 410, to the hospital bed communication device 200 to establish the first wireless communication link 450; and (iii) receive and/or transmit a wireless signal of the second type via the second communication interface 412 which enables locating the hospital bed communication device 200.

As a non-limiting example, one or more wireless nodes such as the wireless node 400 are generally located in a facility such as a hospital or a long-term health care facility comprising multiple hospital beds such as the hospital bed 100. It will be appreciated that the location of the wireless node(s) 400 in the facility is not limited, and depending on the components of the wireless node 400, the wireless node 400 may be located on a wall, ceiling, floor or at least partially within a wall, ceiling, or floor of the facility. As a non-limiting example, one or more wireless nodes such as the wireless node 400 may be located in a room of a hospital.

In some embodiments, the wireless node 400 comprises a battery for receiving electrical power therefrom. Additionally or alternatively, in embodiments where the wireless node 400 connects to an Ethernet network via the third communication interface 414, the wireless node 400 and its third communication interface 414 may be configured to implement a power over Ethernet (POE) Standard where electrical power is passed along data via Ethernet communication links (not shown).

The microcontroller 408 comprises at least one microprocessor (not shown), at least one non-transitory computer-readable storage medium (not shown), and is operatively connected to the different components of the wireless node 400, i.e. the first communication interface 410, the second communication interface 412, and the third communication interface 414. The microcontroller 408 is configured to communicate with and/or operate the other components of the wireless node 400 such as the first communication interface 410, the second communication interface 412, and the third communication interface 414.

Node First Communication Interface

The first communication interface 410 of the wireless node 400 comprises a wireless antenna (not shown) for transmitting and/or receiving a wireless signal of the first type. The first communication interface 410 is configured to connect the wireless node 400 to an electronic device such as the hospital bed first wireless communication interface 232 of the hospital bed communication device 200, via the first wireless communication link 450. The first communication interface 410 enables the wireless node 400 to exchange information via the first wireless communication link 450 by transmitting and receiving data packets 452 to and from the hospital bed first wireless communication interface 232. In alternative embodiments of the present technology, the first communication interface 410 enables only transmission or only reception of data packets 452 via the first wireless communication link 450.

In one embodiment, the first communication interface 410 and the first wireless communication link 450 enable communication based on the Institute of Electrical and Electronics Engineers (IEEE) 802.11 standard, the implementation of which is known in the art. In one embodiment, the first communication interface 410 allows the exchange of information via the same protocol as the third communication interface 414.

In some embodiments, a single wireless antenna may enable reception/or transmission of both the first type of wireless signal and the second type of wireless signal.

In alternative embodiments, the first communication interface 410 may be optional, as a non-limiting example, when the wireless node 400 is only configured to receive the second type of wireless signal to locate the hospital bed 100 and may be connected to a communication network such as the hospital communication network 460 and/or a nurse call system via the third communication interface 414.

Node Second Communication Interface

The second communication interface 412 of the wireless node 400 comprises one or more wireless antennas (not shown) for transmitting and/or receiving wireless signals of the second type. The second communication interface 412 is configured to receive wireless signals of the second type from electronic devices such as the hospital bed communication device 200, which enable locating the hospital bed communication devices. It should be noted that the second type of wireless signal is a wireless signal having a shorter range than the first type of wireless signal, and does not preclude the second communication interface 412 from transmitting different "subtypes" of second type wireless signals (e.g. Bluetooth® and UWB signals).

As a first non-limiting example, the second communication interface 412 may comprise a Bluetooth® communication module, such as a Bluetooth® Low Energy (BLE) communication module. As a second non-limiting example, the second communication interface 412 may comprise an ultra-wideband (UWB) communication module which transmits IEEE 802.15.4 ultra-wideband signals. As a third non-limiting example, the second communication interface 412 may comprise a BLE communication module and an UWB communication module.

In alternative embodiments, a single first antenna may be used for both WiFi® and Bluetooth® communication while a distinct second antenna may be used for UWB communication.

Node Third Communication Interface

The third communication interface 414 of the wireless node 400 is configured to connect the wireless node 400 to a hospital communication network 460 via a central communication link 420. In one embodiment, the third communication interface 414 may be an Ethernet communication interface, and the central communication link 420 may be an Ethernet wire (e.g. RJ45) which connects the wireless node 400 to the hospital communication network 460. The third communication interface 414 enables the wireless node 400 to exchange information over the hospital communication network 460 by transmitting and receiving data packets 462. In other embodiments, the third communication interface 414 is a wireless connection interface which enables connecting the wireless node 400 to the hospital communication network 460 via the central communication link 420.

In some embodiments, the wireless node 400 may further comprises a nurse call interface comprising 37 pins and jack ¼ (not shown) for connecting to a nurse call of a hospital. In some embodiments, the nurse call interface enables connecting the wireless node 400 to a nurse call wirelessly and may be implemented similar to one of the communication interfaces 410, 412, 414.

In some embodiments, the hospital communication network 460 can be implemented as any suitable local area network (LAN), wide area network (WAN), a private communication network or the like. In other embodiments, the hospital communication network 460 is the Internet. It should be expressly understood that implementations for the hospital communication network 460 are for illustration purposes only.

Inquiry Procedure

In one embodiment, the wireless node 400 is configured to execute an inquiry procedure to locate and/or discover other electronic devices having communication interfaces that emit the second type of wireless signal, such as the second communication interface 234 of the hospital bed communication device 200, and where the second type of wireless signals are received via the second communication interface 412 of the wireless node 400. In some embodiments, the wireless node 400 may be configured to determine a location of the hospital bed communication device 200 based on physical and measurable properties of the second type of wireless signal received via the second communication interface 412, including inter alia signal intensity and signal phase. As a non-limiting example, the wireless node 400 may determine an angle of arrival of wireless signals of the second type. It will be appreciated that the inquiry procedure described herein may be executed by the wireless node 400 and/or by another electronic device such as the central computer 470 upon receiving data from the wireless node 400.

The wireless node 400 is configured to receive data packets (such as the second data packets 442) from electronic devices such as the hospital bed communication device 200. The data packets may enable uniquely identifying the electronic devices, such as the hospital bed communication device 200. The wireless node 400 may store the data packets and related information in a storage medium and/or transmit the information over the hospital communication network 460.

In one embodiment, the wireless node 400 receives the second type of wireless signal, i.e. the second data packets 442 in the form of beacons, which are indicative of a location and an identity of the devices broadcasting the beacons. In some embodiments, the wireless node 400 may transmit a specific wireless signal via third communication interface 414, a first communication interface 410, and a second communication interface 412, which may cause the hospital bed communication device 200 to broadcast beacons indicative of their location.

It will be appreciated that the inquiry procedure used to locate patient support apparatuses depends on the implementation of the second type of wireless signal, the second communication interface 412 of the wireless node 400 and the set of communication interfaces 230 of the hospital bed communication device 200.

In one embodiment, the wireless node 400 may transmit the information associating the wireless node 400 and the hospital bed communication device 200 to the central computer 470 over the hospital communication network 460 for storage thereof.

In one embodiment, the wireless node 400 may be connected to other wireless nodes (not shown) via the hospital communication network 460 and receive data from the other wireless nodes such as the wireless network parameters, and determine an approximate location of the hospital beds that are in range.

In one embodiment, the wireless node 400 may be associated with a node location identifier. The node location identifier is indicative of a location of the wireless node 400 in a facility, which may be a hospital for example. In one embodiment, the node location identifier may have been assigned during the initialization of the wireless node 400. As a non-limiting example, the node location identifier may indicate a floor, a room number, and/or a position in the room.

In one embodiment, the first wireless communication link 450 with the wireless node 400 enables the hospital bed communication device 200 to connect to the hospital communication network 460, and transmit data packets to and receive data packets from electronic devices and/or connected over the hospital communication network 460, such as the central computer 470. In another embodiment, the hospital bed communication device 200 may transmit information to the wireless node 400 via the first wireless communication link 450, which may then relay the data packets on the hospital communication network 460.

In one embodiment, upon establishing a wireless communication link with the hospital bed communication device 200, the wireless node 400 is configured to transmit an indication of a successful connection via one or more of the first communication interface 410, the second communication interface 412, and the third communication interface 414 or via an input/output interface. As a non-limiting example, the indication may be in the form of a notification on a display device (such as on a display interface of an electronic device of a health worker (not shown) or a display interface (not shown) of the hospital bed 100 or an audio notification. It is contemplated that the wireless node 400 may also transmit a notification to the central computer 470 and/or remote servers over the hospital communication network 460.

In one embodiment, the wireless node 400 may associate the wireless communication parameters or fingerprints determined from second data packets 442 received via the second communication interface 412, to information received via the first communication interface 410, when the hospital bed communication device 200 is in the connected state 310 and has established the first wireless communication link 450.

In some embodiments, the wireless node 400 further comprises a dip switch and relays (not shown) for configuration to the nurse call of the hospital, and a micro USB interface (not shown) to enable configuration of the wireless node 400. The wireless node 400 may further comprise visual indicators, such as RGB LEDs to indicate a connection status of the wireless node 400.

Central Computer

The central computer 470 is connected to the hospital communication network 460 via a respective communication link (not numbered).

The central computer 470 is an electronic device that may be implemented as a general-purpose computer or server. The central computer 470 comprises inter alia a processor (not shown), storage mediums, and one or more communication interfaces (not shown) for connecting to the hospital communication network 460. The central computer 470 further comprises a display interface (not shown), an input/output interface (not shown) such as touchpad, a keyboard and a mouse, etc.

The central computer 470 is configured to inter alia: (i) maintain a list of wireless nodes such as the wireless node 400, where each wireless node may be associated with a particular or specific hospital bed communication device such as the hospital bed communication device 200 and a location; (ii) receive data from the wireless nodes over the hospital communication network 460; and (iii) determine an approximate location of one or more hospital beds based on information received from the wireless nodes, such as the wireless node 400.

In some embodiments, the central computer 470 is configured to: (i) receive data related to hospital beds and patients, such as configuration parameters, approximate locations and status of the hospital bed 100; and (ii) provide a graphical interface 475 comprising a dashboard for visualization of the data related to the hospital beds and patients including the configuration parameters, the approximate locations and status of the hospital beds. Additionally, the graphical interface 475 may comprise a control interface which enables control of the one or more of the configuration parameters of the hospital bed 100, the hospital bed communication device 200 and the wireless node 400.

In some embodiments, the central computer 470 may transmit at least a portion of the data related to hospital beds and patients and the graphical interface 475 comprising the dashboard to other electronic devices (not shown) such as smartphones or tablets of health workers. Additionally, the graphical interface 475 transmitted to the other electronic devices (not shown) may comprise the control interface to enable healthcare workers to enable control of the one or more of the configuration parameters of the hospital bed 100, the hospital bed communication device 200 and the wireless node 400.

Non-limiting examples of data related to the hospital bed 100 and the patient comprise one or more of: nurse call alarm, bed exit alarm, brake status alarm, siderails status alarm, backrest status alarm, height status alarm, fall risk prevention log events, patient weight, center of mass, bed backrest angle, bed height, bed width, and maintenance data.

In one embodiment, the central computer 470 is configured to determine an approximate location of one or more hospital beds based on the association information received from the wireless nodes via their respective third communication interfaces.

In some embodiments, the central computer 470 determines an approximate location of one or more hospital beds based on an inquiry response rate (IRR) procedure executed by a wireless node such as the wireless node 400. The IRR is a percentage of inquiry responses to total inquiries which are replied by an electronic device in discovery mode, and transmitted by the wireless node 400 that is located in a specific distance from the electronic device in discovery mode.

Having described the first hospital bed communication system 300 in accordance with some embodiments, a second hospital communication system 500, in accordance with some non-limiting embodiments of the present technology, will now be described with reference to FIG. 3.

Second System

Much like the system 300, the second hospital bed communication system 500 or system 500 comprises inter alia the hospital bed 100 and the associated hospital bed communication device 200, a wireless node 550, and a central computer 470 connected to the wireless node 550 over a hospital communication network 460.

Much like the wireless node 400, the wireless node 550 comprises inter alia a microcontroller 508, a third communication interface 514, a first communication interface 510, and a second communication interface 512, and further comprises a power output interface 502, a power input interface 504, and a current sensor 506.

The microcontroller 508, the third communication interface 514, the first communication interface 510, and the second communication interface 512 are implemented in a manner similar to the microcontroller 408, the first communication interface 410, the second communication interface 412, and the third communication interface 414 respectively.

The wireless node 550 is configured to inter alia: (i) connect to an electrical power source 340 via the power output interface 502 to receive electrical power therefrom; (ii) connect to the hospital communication network 560 and exchange data packets 462 over the hospital communication network 460; (iii) receive an electrical connection from the electrical connection wire 192 of the hospital bed 100 and provide power to the hospital bed 100 via the power input interface 504; (iv) connect to the hospital bed communication device 200 associated with the hospital bed 100 via the first wireless communication link 450; (v) receive and/or transmit a wireless signal of the second type via the second communication interface 512. In one embodiment, the wireless node 550 is configured to transmit data via the electrical connection wire 192 to the hospital bed communication device 200.

The power output interface 502 connects the wireless node 550 to a power outlet or power source 340 to receive electrical power therefrom. As a non-limiting example, the power source 340 may connect to an electrical grid of a facility such as a hospital or health care center. It should be noted that there may be a wireless node such as the wireless node 550 for every power outlet in a facility where a patient support apparatus such as the hospital bed 100 may be positioned. As a non-limiting example, the power output interface 502 may comprise an AC/DC converter (110/220 V AC to 5V DC) and a tension regulator of 5V to 3.3V.

The power input interface 504 is configured to receive a wired electrical connection of an electrical apparatus, such as the electrical connection wire 192 of the hospital bed 100 of FIG. 1. The power input interface 504 transmits electrical power to the hospital bed 100. As a non-limiting example, the power input interface 504 is in the form of a 110/220V AC-10 A power outlet to connect to the hospital bed 100. In one embodiment, the power input interface 504 comprises or is coupled to a current sensor 506 for detecting and measuring electrical power, i.e. current, consumed by a device that is electrically connected to the power input interface 504. In one embodiment, the electrical sensor is an integrated circuit Hall-effect current sensor that provides analog output voltage signals proportional to the applied current. The current sensor 506 enables detecting that a device such as the hospital bed 100 has been connected to the power input interface 504 based on the current consumption. It should be noted that the current sensor 506 does not need to be present in every embodiment of the present technology. In one embodiment, the power input interface 504 implements universal asynchronous receiver-transmitter (UART) components for serial communication via the electrical connection wire 192 with the hospital bed communication device 200. Thus, the wireless node 550 may receive and/or transmit data via the electrical connection wire 192 to the hospital bed communication device 200.

Inquiry Response Rate

In one embodiment, the wireless node 550 is configured to execute an inquiry response rate (IRR) procedure to discover electronic devices transmitting the second type of wireless signal, such as the hospital bed communication device 200. The IRR procedure frequency hops though a specified subset of frequencies to find electronic devices in range and associated with hospital beds that are discoverable.

The IRR procedure enables the wireless node 550 to receive and transmit, via the second communication interface 512, a plurality of data packets referred to as second data packets 442.

In one embodiment, during the IRR procedure, the wireless node 550 transmits, via the second communication interface 512, two inquiry data packets on two different frequencies during a given timeslot. A predetermined period of time later, the wireless node 550 listens on the same frequency. The wireless node 550 receives one or more frequency hop synchronization (FHS) packets from one or more electronic devices such as the hospital bed communication device 200, where each FHS packet includes a device address, a clock offset and a cyclic redundancy check (CRC) code. The wireless node 550 then determines the IRR.

In one embodiment the wireless node 550 may determine wireless communication parameters such a spatial density of hospital beds in a given area based on: (i) receiving the second type of wireless signal from electronic devices such as the hospital bed communication device 200; and (ii) a number of times the second type of wireless signal has been received from electronic devices such as the hospital bed communication device 200.

The wireless node 550 may store in memory and/or transmit the wireless communication parameters determined based on the second type of wireless signal measured via the second communication interface 512. The wireless communication parameters or fingerprints may allow identifying and approximately locating the hospital bed communication device 200.

In one embodiment, the wireless node 550 may be preconfigured to establish a connection via the first wireless communication link 450 with the hospital bed communication device 200 upon the hospital bed 100 being electrically connected to the power input interface 404 of the wireless node 550. The manner in which the wireless node 550 establishes the first wireless communication link 450 to connect to hospital bed communication device 200 is not limited. In one embodiment, the wireless node 550 activates the first communication interface 510 in response to the hospital bed 100 being electrically connected to the power input interface 504 via the electrical connection wire 192. In one embodiment, the wireless node 550 may deactivate the first communication interface 510 when there is no electrical connection to the power input interface 504.

In one embodiment, the wireless node 550 is configured to detect and measure, via the current sensor 506, electrical power consumed by a device that is electrically connected to the power input interface 504. Since a range of consumption of electrical power by a hospital bed such as the hospital bed 100 is known, the wireless node 550 may determine that the power input interface 504 has been electrically connected to the hospital bed 100 via the electrical connection wire 192 based on a threshold. In response to determining that the electrical power consumption is above the threshold, the wireless node 550 may activate the first communication interface 510 to connect and establish the first wireless communication link 450 with the hospital bed communication device 200. In one embodiment, in response to determining that the electrical power consumption is above the threshold, the wireless node 550 may transmit a unique password to the hospital bed communication device 200 via the electrical connection wire 192, such that the hospital bed communication device 200 receives the unique password, and transmits, via the first communication interface 510, the unique password to the wireless node 550, which authenticates the hospital bed communication device 200 and establishes the first wireless communication link 450 with the wireless node 550. To enable transmission of data such as the unique password via the electrical connection wire 192, the hospital bed communication device 200, the wireless node 550, and the electrical connection wire 192 may implement universal asynchronous receiver/transmitter (UART) communication.

In one embodiment, the wireless node 550 and the electrical connection wire 192 of the hospital bed 100 use power-line communication (PLC) for data transmission. Once the electrical connection wire 192 has been connected to the power input interface 504, information may be exchanged between the hospital bed communication device 200 and the wireless node 550 via PLC. The wireless node 550 may transmit a unique password to the hospital bed communication device 200 via the electrical connection wire 192. The hospital bed communication device 200 may transmit, via the first communication interface 510, the unique password to the wireless node 550, which authenticates the hospital bed communication device 200 and establishes the first wireless communication link 450 with the wireless node 550.

In one embodiment, the wireless node 550 is configured using the Wi-Fi® Protected Setup (WPS®) Standard to connect to the hospital bed communication device 200 in response to receiving the electrical connection wire 192 from the hospital bed 100 in the power input interface 504.

In an alternative embodiment, the wireless node 550 may determine that the electrical connection wire 192 of the hospital bed 100 has been connected to the power input interface 504 by using a radio-frequency identification (RFID) reader and a tag. As a non-limiting example, a RFID reader may be installed on the wireless node 550 and a RFID tag may be installed on the electrical connection wire 192, such that when the electrical connection wire 192 is connected to the power input interface 504, the RFID reader captures radio waves from the RFID tag, which enables determining that the hospital bed 100 has been electrically connected to the power input interface 504. In response to determining that the hospital bed 100 has been electrically connected to the power input interface 504, the wireless node 550 may activate the first communication interface 510 to connect to the hospital bed communication device 200 and establish the first wireless communication link 450 therewith.

In an alternative embodiment, the wireless node 550 may include a mechanical switch to detect that the electrical connection wire 192 has been connected to the power input interface 504.

In one embodiment, to ensure that the wireless node 550 always establishes the first wireless communication link 450 with the hospital bed communication device 200 of the hospital bed 100 that has been electrically connected to the wireless node 550, and not the communication device (not shown) of another hospital bed (not shown) that is in range, the wireless node 550, upon having established the first wireless communication link 450, is configured to transmit a unique password to the hospital bed communication device 200 such that upon the hospital bed 100 being electrically disconnected from the wireless node 550 and electrically reconnected to the wireless node 550, the hospital bed communication device 200 is the only device that may establish the first wireless communication link 450 with the wireless node 550 by authentication via the unique password. In one embodiment, the wireless node 550 may transmit a different unique password every time the first wireless communication link 450 is established with the hospital bed communication device 200 such that other devices that are not electrically connected to the wireless node 550 and have not received the unique password are prevented from connecting to the wireless node 550. As a non-limiting example, such a situation may occur after a power outage, where two or more hospital beds may be simultaneously reconnected by health workers to their respective wireless nodes, and where a given patient device of a hospital bed tries to connect and establish the first wireless communication link 450 to a wireless node to which it is not electrically connected.

In one embodiment, the first wireless communication link 450 with the wireless node 550 enables the hospital bed communication device 200 to connect to the hospital communication network 460, and transmit and receive data packets to electronic devices such as the central computer 470 connected over the hospital communication network 460. In another embodiment, the hospital bed communication device 200 may transmit information to the wireless node 550 via the first wireless communication link 450, which may then relay the data packets on the hospital communication network 460.

In one embodiment, upon establishing a wireless communication link with the hospital bed communication device 200, the wireless node 550 is configured to transmit an indication of a successful connection. As a non-limiting example, the indication may be in the form of a notification on a display device (such as on the display interface (not shown) of the hospital bed 100 or a display interface of an electronic device of a health worker (not shown)) or an audio notification. It is contemplated that the wireless node 550 may also transmit a notification to the central computer 470 over the hospital communication network 460.

In one embodiment, the wireless node 550 may associate the wireless communication parameters or fingerprints determined from second data packets 442 received via the second communication interface 512, when the hospital bed 100 was not electrically connected to the wireless node 550 and the hospital bed communication device 200, to information received via the first communication interface 510, when the hospital bed 100 is electrically connected to the wireless node 550.

Thus, once the hospital bed 100 has been electrically connected to the wireless node 550 and the first wireless communication link 450 has been established, the wireless node 550 may determine that the second data packets 442 were received from the hospital bed communication device 200 and associated with the hospital bed communication device 200. If the hospital bed 100 is electrically disconnected from the wireless node 550, the hospital bed communication device 200 may activate the second wireless communication interface 234 to transmit the second type of wireless signal and the wireless node 550 may receive the second data packets 442 and identify the hospital bed communication device 200. The hospital bed 100 associated with the hospital bed communication device 200 may be approximately located based on the wireless communication parameters.

It will be appreciated that the system 500 enables automatically establishing the first wireless communication link 450 between the hospital bed communication device 200 to the wireless node 550 once the hospital bed 100 has been electrically connected to the wireless node 550, without requiring human intervention. In some embodiments, healthcare worker having an electronic device (e.g. smartphone or tablet) connected to the wireless node 550 and/or the hospital communication network 460 may thus receive and view connection status of hospital bed communication devices in real-time.

Having described the hospital bed 100, the hospital bed communication device 200, the system 300 and the system 500, a procedure for locating hospital beds will now be described.

Hospital Bed Location Procedure

Figure 4:
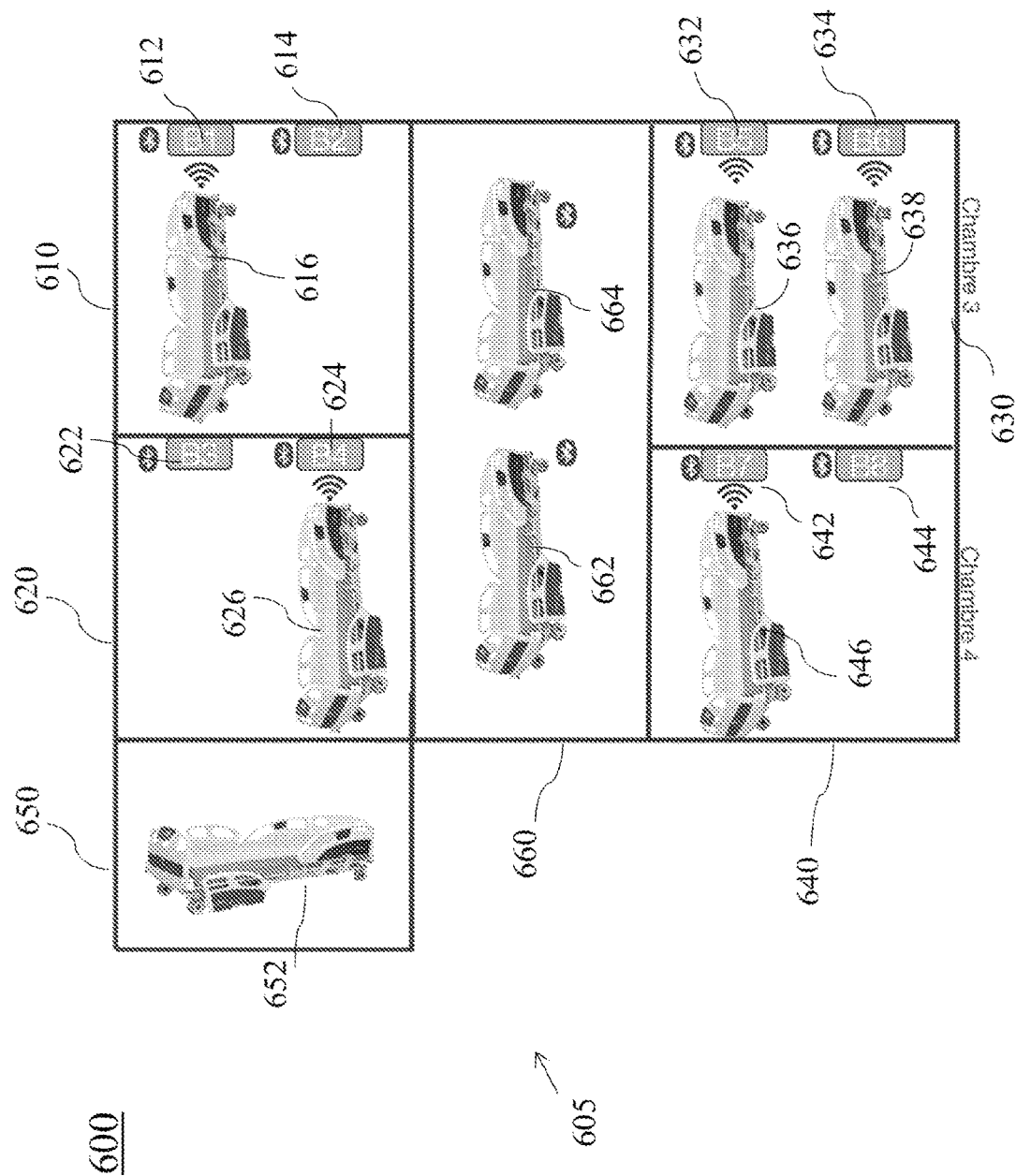
FIG. 4 depicts a schematic diagram of a patient apparatus location determination procedure on a hospital floor in accordance with non-limiting embodiments of the present technology.
Figure 5:
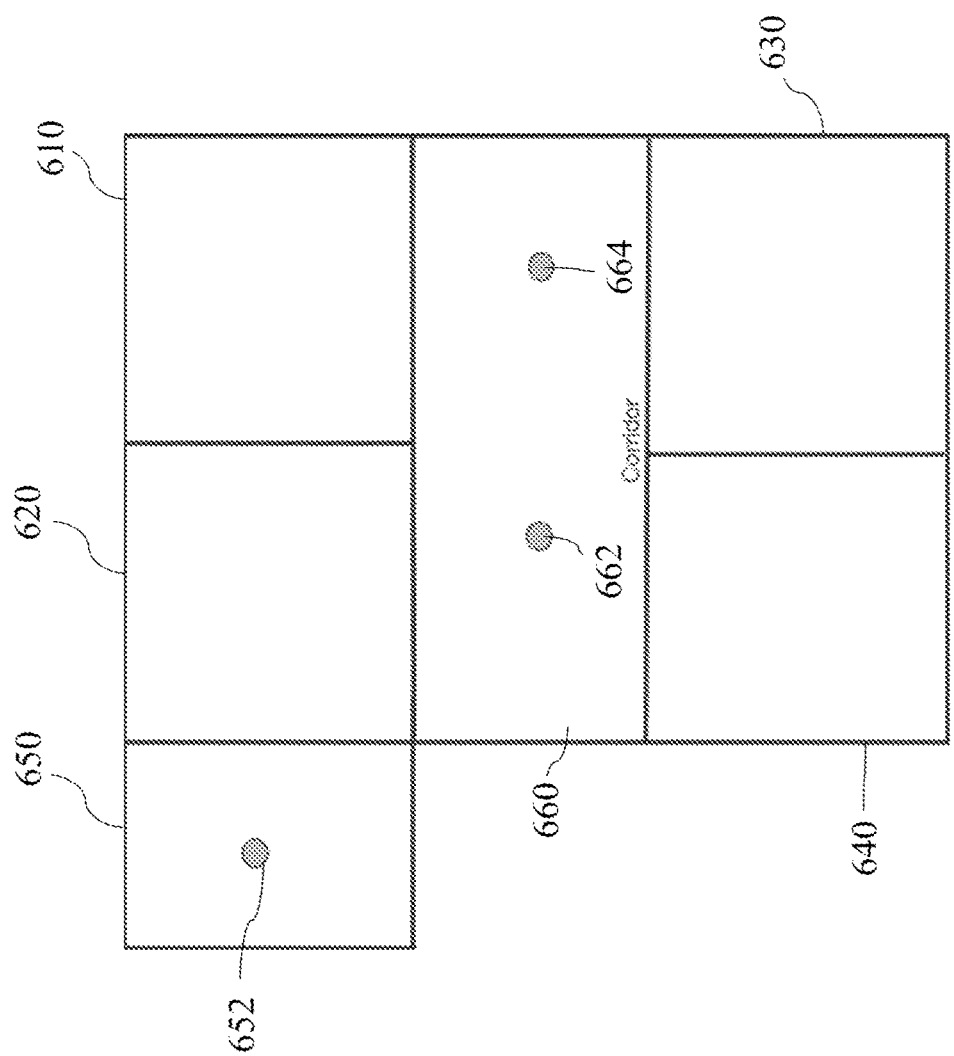
FIG. 5 depicts a schematic diagram of hospital beds located on a hospital floor in accordance with non-limiting embodiments of the present technology.

With reference to FIG. 4 and FIG. 5 a hospital bed location determination procedure 600 will be described in accordance with one or more non-limiting embodiments of the present technology.

A section of a health facility floor 605 or hospital floor 605 is illustrated. The hospital floor 605 comprises a first room 610, a second room 620, a third room 630, a fourth room 640, a maintenance room 650 and a hallway 660.

The first room 610 comprises: a first wireless node 612, a second wireless node 614, and a first hospital bed 616 comprising a first hospital bed communication device (not separately numbered) associated therewith. The first hospital bed 616 is electrically connected to the first wireless node 612 and is in the connected state 310.

The second room 620 comprises: a third wireless node 622, a fourth wireless node 624, and a fourth hospital bed 626 comprising a fourth hospital bed communication device (not separately numbered) associated therewith. The fourth hospital bed 626 is electrically connected to the fourth wireless node 624 and is in the connected state 310.

The hallway 660 comprises a second hospital bed 662 and a third hospital bed 664. The hallway 660 does not have any wireless nodes, and the third hospital bed 664 and the second hospital bed 662 are in the disconnected state 305. It should be noted that the third hospital bed 664 and the second hospital bed 662 have been previously electrically connected respectively to a wireless node, such as the third wireless node 622 and the second wireless node 614.

The third room 630 comprises a fifth wireless node 632, a sixth wireless node 634, a fifth hospital bed 636 and a sixth hospital bed 638. The fifth hospital bed 636 comprises a fifth hospital bed communication device (not separately numbered) associated therewith and is electrically connected to the fifth wireless node 632 and is in the connected state 310. The sixth hospital bed 638 comprises a fifth hospital bed communication device (not separately numbered) associated therewith and is electrically connected to the sixth wireless node 634 and is in the connected state 310.

The fourth room 640 comprises a seventh wireless node 642, an eighth wireless node 644, and a seventh hospital bed 646. The seventh hospital bed 646 comprises a seventh hospital bed communication device (not separately numbered) associated therewith and is electrically connected to seventh wireless node 642 and is in the connected state 310.

The maintenance room 650 comprises an eighth hospital bed 652 comprising a eighth hospital bed communication device (not separately numbered) associated therewith. It should be noted that the eighth hospital bed 652 has been previously electrically connected to a wireless node, such as the eighth wireless node 644 from which it has been disconnected.

The first wireless node 612, the second wireless node 614, the third wireless node 622, the fourth wireless node 624, the fifth wireless node 632, the sixth wireless node 634, the seventh wireless node 642, and the eighth wireless node 644 are connected over the hospital communications network 460 to exchange information with the central computer 470 (not shown in FIG. 4). The wireless nodes 612, 614, 622, 624, 632, 634, 642, 644 are configured in a manner similar to the wireless node 550.

The first hospital bed 616, the second hospital bed 662, the third hospital bed 664, the fourth hospital bed 626, the fifth hospital bed 636, the sixth hospital bed 638, the seventh hospital bed 646, and the eighth hospital bed 652 are similar to the hospital bed 100 and comprise respective associated hospital bed communication device similar to the hospital bed communication device 200.

Each wireless node nodes 612, 614, 622, 624, 632, 634, 642, 644 is configured to execute an IRR procedure via its respective second communication interface 412, and transmits information to the central computer 470.

In one embodiment, the wireless nodes 612, 614, 622, 624, 632, 634, 642, 644 may execute the IRR procedure upon receiving an indication from the central computer 470. In another non-limiting embodiment, only a portion of the wireless nodes 612, 614, 622, 624, 632, 634, 642, 644 may execute the IRR procedure. The IRR procedure may be executed during the hospital bed location determination procedure 600.

In one embodiment, the hospital bed location determination procedure 600 may be executed by the central computer 470 (FIG. 3). In another embodiment, the hospital bed location determination procedure 600 may be executed by a wireless node such as one of the wireless nodes 612, 614, 622, 624, 632, 634, 642, 644.

As a non-limiting example, a healthcare worker may want to know a location of the hospital beds 616, 662, 664, 626, 636, 638, 646, 652 on the hospital floor 605 at a given moment in time and use the central computer 470 to do so. The healthcare worker may interact with a mouse and keyboard (not shown) or a touchscreen (not shown) of the central computer 470, which may cause execution of the hospital bed location determination procedure 600.

In another non-limiting example, the central computer 470 may be configured to execute the hospital bed location determination procedure 600 to determine the approximate locations of the hospital beds 616, 662, 664, 626, 636, 638, 646, 652 at predetermined intervals of time, such as every 3 hours.

With each of the hospital beds 616, 662, 664, 626, 636, 638, 646, 652 having been previously electrically connected to a respective wireless node 612, 614, 622, 624, 632, 634, 642, 644 and established a respective communication link (not shown), an association based on the second type of wireless signal received via the respective second communication interfaces and each of the hospital beds 616, 662, 664, 626, 636, 638, 646, 652 may be known.

The association may be included in wireless network parameters or fingerprints of each of the hospital beds 616, 662, 664, 626, 636, 638, 646, 652 stored in a computer-readable storage medium. The wireless network parameters may have been determined by one or more of the wireless nodes 612, 614, 622, 624, 632, 634, 642, 644.

In one embodiment, the wireless networks parameters may be indicative of a density of hospital beds in a section of the hospital floor 605. The density of hospital beds in the section of hospital floor 605 may be determined based on: (i) wireless nodes receiving the second type of wireless signal from hospital beds in the disconnected state 305; and (ii) a number of times the wireless nodes have received the second type of wireless signal from the hospital beds in the disconnected state 305.

Thus, a hospital bed that is in the disconnected state 305, such as the second hospital bed 662, the third hospital bed 664 and the eighth hospital bed 652 may be approximately located. As stated above, in the disconnected state 305, each of the second hospital bed 662, third hospital bed 664 and the eighth hospital bed 652 transmit and receive the second type of wireless signal via their respective second wireless communication interface 234.

One or more of the wireless nodes 612 612, 614, 622, 624, 632, 634, 642, 644 may receive the second type of wireless signal from one or more of the second hospital bed 662, third hospital bed 664 and the eighth hospital bed 652, and determine an IRR. The IRR may be in the form of current wireless network parameters. The current wireless network parameters may be transmitted to the central computer 470. The IRR procedure may be executed at predetermined periods of time.

The central computer 470, based on the previously known wireless network parameters and the current known wireless network parameters received from the wireless node 612 612, 614, 622, 624, 632, 634, 642, 644 may determine the approximate location of at least one of the second hospital bed 662, the third hospital bed 664 and the eighth hospital bed 652. In one embodiment, the central computer 470 is configured to compare the previous wireless network parameters and the current wireless network parameters.

The central computer 470 compares the previously known wireless network parameters with the IRR received from the wireless node 612 612, 614, 622, 624, 632, 634, 642, 644 using a statistical method to determine the locations. In one embodiment, the central computer 470 compares the previously known wireless network parameters with the IRR received from the wireless node 612 612, 614, 622, 624, 632, 634, 642, 644 using the Kullback-Liebler (KL) measure, or a Jensen-Shannon (JS) distance measure.

Having determined the approximate locations of each of the second hospital bed 662, the third hospital bed 664 and the eighth hospital bed 652, the central computer 470 outputs the locations of the second hospital bed 662, the third hospital bed 664 and the eighth hospital bed 652.

In one embodiment, the central computer 470 may display for example on a display screen, the approximate locations of the second hospital bed 662, the third hospital bed 664 and the eighth hospital bed 652 on the hospital floor 605, as depicted in FIG. 5.

Having described the hospital bed location determination procedure 600, which may be used to locate hospital beds configured according to the system 300 and/or the system 500, other non-limiting embodiments of hospital bed communication systems will now be described with reference to FIG. 6 and FIG. 7.

Third System

Figure 6:
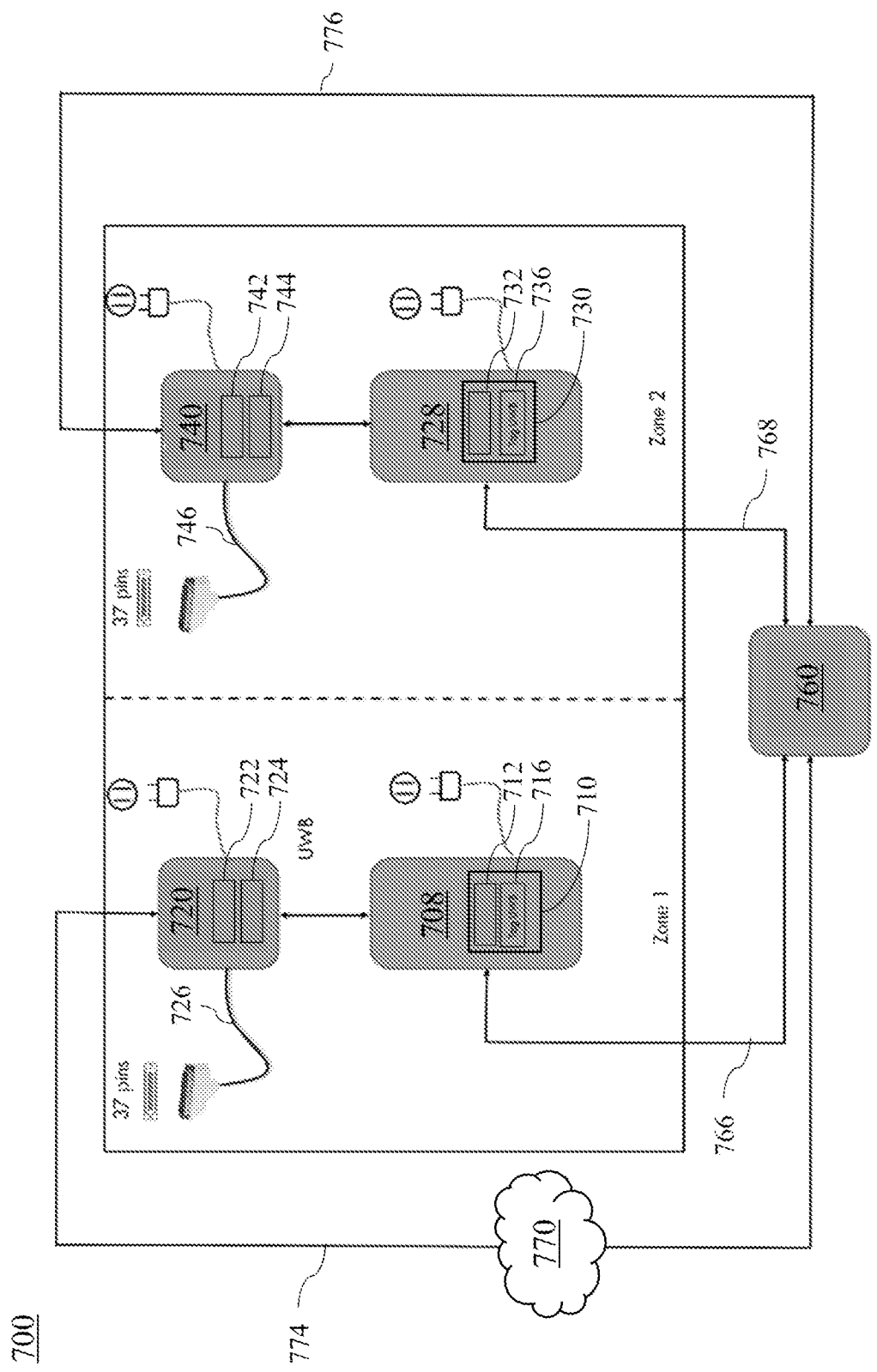
FIG. 6 depicts a schematic diagram of a third hospital bed communication system in accordance with non-limiting embodiments of the present technology.
Figure 7:
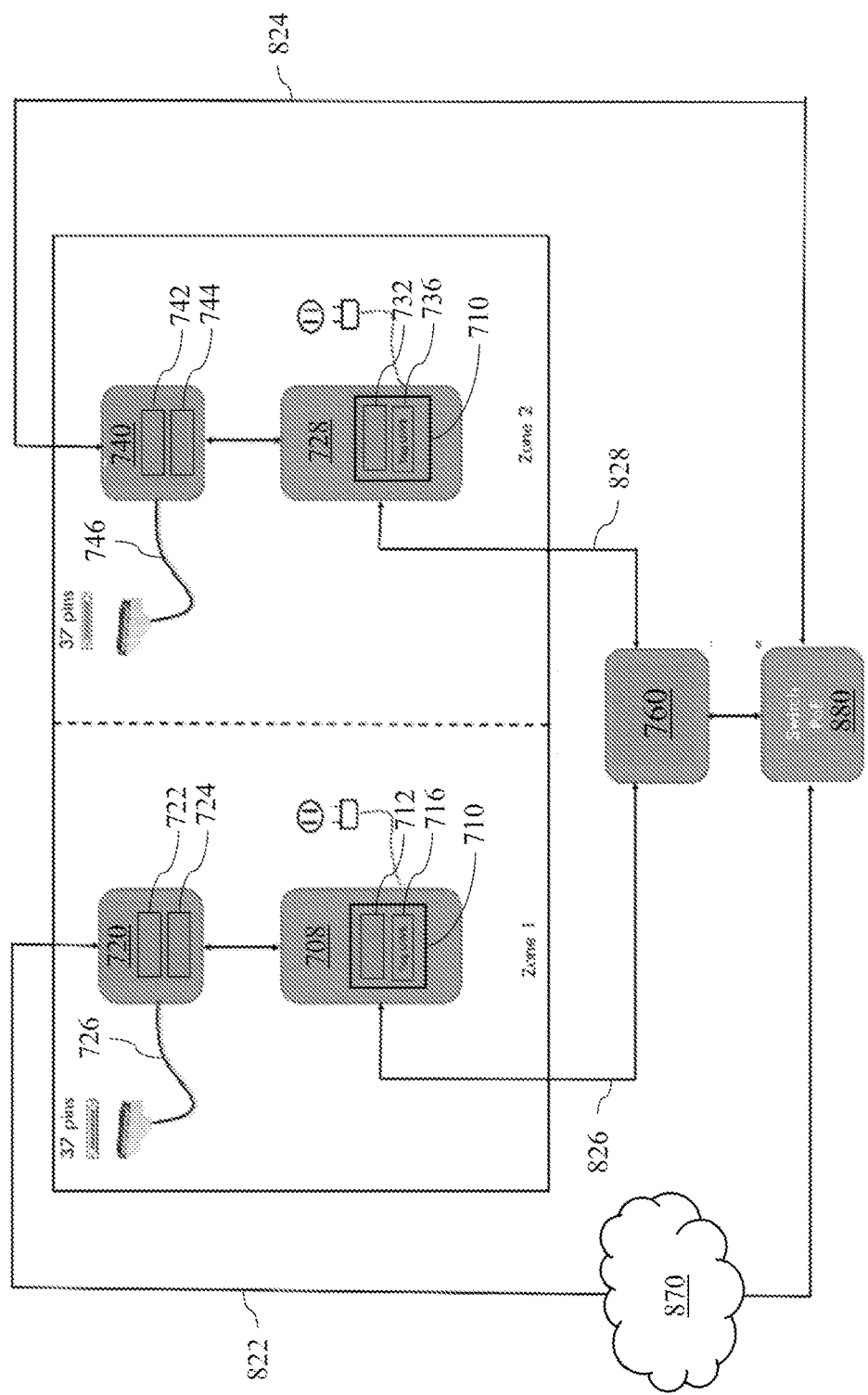
FIG. 7 depicts a schematic diagram of a fourth hospital bed communication system in accordance with non-limiting embodiments of the present technology.

FIG. 6 depicts a schematic diagram of a third hospital bed communication system 700 in accordance with non-limiting embodiments of the present technology.

The third hospital bed communication system 700 comprises a first hospital bed 708 associated with a first hospital bed communication device 710 and a first wireless node 720, a second hospital bed 728 associated with a second hospital bed communication device 730, a second wireless node 740 and a central server 760.

The first hospital bed 708 and the second hospital bed 728 are similar to the hospital bed 100, and the first hospital bed communication device 710 and the second hospital bed communication device 730 are similar to the hospital bed communication device 200. The first hospital bed communication device 710 and the second hospital bed communication device 730 each comprise inter alia (i) a respective first communication interface 712, 732 for transmitting the first type of wireless signal; and (ii) a respective second communication interface 716, 736 for transmitting a second type of wireless signal in the form of UWB signal.

The first hospital bed communication device 710 and the second hospital bed communication device 730 are connected to central server 760 over respective wireless communication links 766, 768 via the first communication interface 712, 732.

The first wireless node 720 and the second wireless node 740 each comprise inter alia: (i) a respective third communication interface 722, 742 for transmitting a signal of the first type for connecting the wireless nodes 720, 740 to a communication network 770 comprising the central server 760 via communication links 774, 776; (ii) a respective second communication interface 724, 744 for transmitting and receiving a wireless signal of the second type comprising a UWB signal; and (iii) a respective nurse call interface 726, 746 for connecting to a nurse call system. The first wireless node 720 and the second wireless node 740 are respectively connected to a power outlet for receiving electrical power therefrom via a respective electrical wire connection (not numbered).

In some embodiments, the respective third communication interface 722, 742 are wired Ethernet interfaces.

In some embodiments, the nurse call interface 726, 746 may be implemented as wireless communication interfaces.

The first wireless node 720 and the second wireless node 740 detect respectively a location of the hospital beds 710, 730 in proximity via the respective second communication interface 724, 744 which receives UWB signals transmitted by the respective second communication interface 716, 736 of the first hospital bed communication device 710 and the second hospital bed communication device 730.

The first wireless node 720 and the second wireless node 740 each transmit a respective position of the hospital beds 710, 730 via the respective third communication interface 722, 742.

The first hospital bed communication device 710 and the second hospital bed communication device 730 each receive an indication of their respective positions from the central server 760 via the respective first communication interfaces 712, 732. In response, the hospital beds 710, 730 transmit nurse call indications to the central server 760 via the respective first communication interfaces 712, 732. The central server 760 transmits the nurse call indications to the wireless nodes 720, 740, which receive and transfer the nurse call to a respective nurse call interface 726, 736 to a 37-pin connector.

Fourth System

Another implementation of a hospital bed communication system will now be described with reference to FIG. 7, which depicts a schematic diagram of the fourth hospital bed communication system 800 in accordance with non-limiting embodiments of the present technology.

The fourth hospital bed communication system 800 is similar to the third hospital bed communication system 700, however the first wireless node 720 and the second wireless node 740 are not connected to a power outlet for receiving electrical power therefrom via a respective electrical wire connection, and instead receive electrical power and data using the power over Ethernet (PoE) standard via respective PoE links 822, 824 which are connected to a PoE switch 880 and connected to the third communication interface 722, 742 over a PoE communication network 870. The hospital beds 710, 730 are connected to the central server 760 via respective communication links 826, 828 using the respective first communication interfaces 712, 732.

Having described non-limiting embodiments of the hospital bed 100, the hospital bed communication device 200 and hospital bed communication systems 300, 500, 700, 800, methods of connecting a patient support apparatus or hospital bed to a wireless node will now be described.

Method Description

Figure 8:
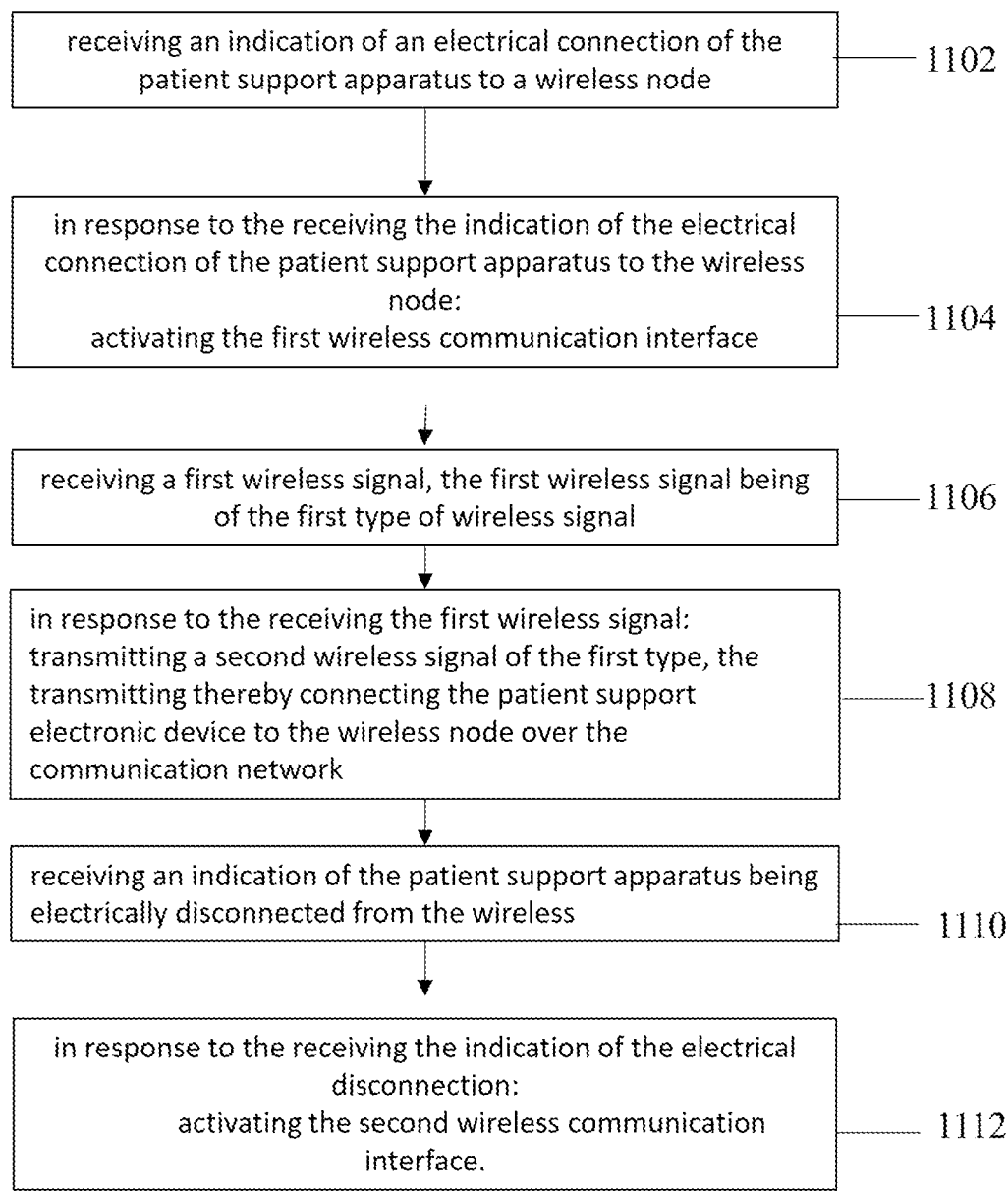
FIG. 8 depicts a flow chart of a method of connecting a patient support apparatus to a wireless node in accordance with non-limiting embodiments of the present technology.

FIG. 8 depicts a flow chart of a method 1100 of connecting a patient support apparatus to a wireless node in accordance with non-limiting embodiments of the present technology.

The method 1100 is executed by the hospital bed communication device 200 associated with the hospital bed 100. In one embodiment, the hospital bed communication device 200 is in the disconnected state 305. The method 1100 is executed to connect the hospital bed 100 to the wireless node 550.

The method 1100 begins at step 1102.

STEP 1102: receiving an indication of an electrical connection of the patient support apparatus to a wireless node At step 1102, the hospital bed communication device 200 receives an indication of an electrical connection of the hospital bed 100 to the wireless node 550 via the electrical connection wire 192. The wireless node 550 is connected to the power source 340. In one embodiment, the hospital bed communication device 200 is operatively connected to the control unit 180 of the hospital bed 100 and receives the indication therefrom. In one embodiment, the wireless node 550 and the hospital bed communication device 200 use PLC to exchange data over the electrical connection wire 192. In one embodiment, the hospital bed communication device 200 and the wireless node 550 use UART to exchange data over the electrical connection wire 192. In one embodiment, the indication includes a unique password generated by the wireless node 550. A different unique password may be generated every time by the wireless node 550 when it receives an electrical connection of a hospital bed 100.

The method 1100 advances to step 1104.

STEP 1104: in response to the receiving the indication of the electrical connection of the patient support apparatus to the wireless node:
activating the first wireless communication interface At step 1104, in response to the indication of the electrical connection, the hospital bed communication device 200 activates the first wireless communication interface 232. In some embodiments, the hospital bed communication device 200 deactivates the second wireless communication interface 234.

The method 1100 advances to step 1106.

STEP 1106: receiving a first wireless signal, the first wireless signal being of the first type of wireless signal At step 1106, the hospital bed communication device 200 receives, from the wireless node 550, a first wireless signal of the first type via the first wireless communication interface 232

The method 1100 advances to step 1108.

STEP 1108: in response to the receiving the first wireless signal:
transmitting a second wireless signal of the first type, the transmitting thereby connecting the patient support electronic device to the wireless node over the communication network At step 1108, in response to the receiving of the first wireless signal of the first type, the hospital bed communication device 200 transmits, via the first wireless communication interface 232, a second wireless signal of the first type. By receiving the first wireless signal and the second wireless signal the hospital bed communication device 200 forms the first wireless communication link 450 with the wireless node 550. In one embodiment, the second signal of the first type includes the unique password of the wireless node 550 received via the electrical connection wire 192, which enables authenticating the hospital bed communication device 200 with the wireless node 550 and establish the first wireless communication link 450. The unique password prevents hospital bed communication devices (not shown) associated with hospital beds (not shown) that are not electrically connected to the wireless node 550 from connecting to the wireless node 550 via the first type of signal instead of the hospital bed communication device 200 currently connected thereto.

The method 1100 advances to step 1110.

STEP 1110: receiving an indication of the patient support apparatus being electrically disconnected from the wireless At step 1110, the hospital bed communication device 200 receives an indication that the hospital bed 100 has been electrically disconnected from the wireless node 550. The hospital bed communication device 200 may receive the indication from the control unit 180 of the hospital bed 100.

The method 1100 advances to step 1112.

STEP 1112: in response to the receiving the indication of the electrical disconnection:
activating the second wireless communication interface.

At step 1112, in response to the indication that the hospital bed 100 has been electrically disconnected from the wireless node 550, the hospital bed communication device 200 activates the second wireless communication interface 234. In some embodiments, the hospital bed communication device 200 deactivates the first wireless communication interface 232.

The method 1100 may then end.

Figure 9:
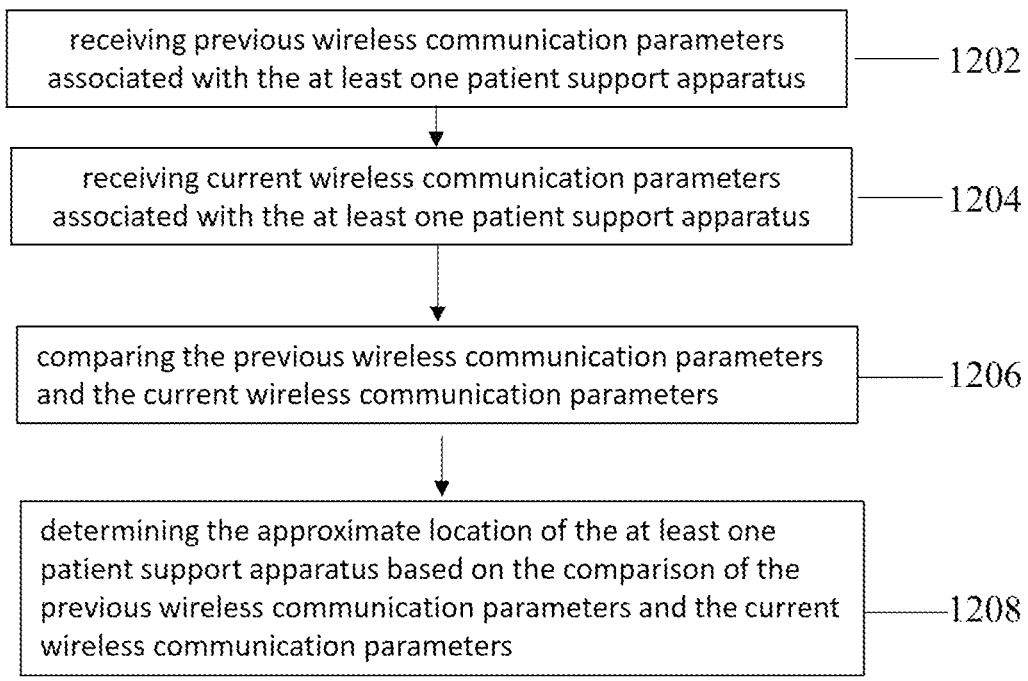
FIG. 9 depicts a flow chart of a method of determining an approximate location of a patient support apparatus in accordance with non-limiting embodiments of the present technology.

FIG. 9 depicts a flow chart of a method 1200 of determining an approximate location of a patient support apparatus in accordance with non-limiting embodiments of the present technology.

The method 1200 may be executed by a processor of a wireless node such as the wireless node 400, 550, or by an electronic device such as the central computer 470. The patient support apparatus may be the hospital bed 100.

The method 1200 begins at step 1202.

STEP 1202: receiving previous wireless communication parameters associated with the at least one patient support apparatus At step 1202, previous wireless communication parameters associated with the hospital bed 100 are received. In one embodiment, the previous wireless communication parameters have been determined by at least one of a plurality of wireless nodes by previously receiving a first type and a second type of wireless signal from the hospital bed 100. The previous wireless communications parameters are indicative of a past spatial density of hospital beds in the facility. The previous wireless communication parameters may have been determined based on an IRR procedure. In one embodiment, the previous wireless communication parameters have been determined by the wireless node 550.

The method 1200 advances to step 1204.

STEP 1204: receiving current wireless communication parameters associated with the at least one patient support apparatus At step 1204, current wireless communication parameters associated with the hospital bed 100 are received. In one embodiment the current wireless communication parameters have been determined by at least a portion of the plurality of wireless nodes by receiving the second type of wireless signal from at least one patient support apparatus. In one embodiment, the current wireless communication parameters are indicative of a current spatial density of hospital beds in the facility. The current wireless communication parameters may have been determined based on an IRR procedure executed by one or more of the plurality of wireless nodes. In one embodiment, the current wireless communication parameters have been determined by the wireless node 550.

The method 1200 advances to step 1206.

STEP 1206: comparing the previous wireless communication parameters and the current wireless communication parameters At step 1206, the previous wireless communication parameters and the current wireless communication parameters are compared.

The method 1200 advances to step 1208.

STEP 1208: determining the approximate location of at least one patient support apparatus based on the comparison of the previous wireless communication parameters and the current wireless communication parameters At step 1208, the approximate location of the hospital bed 100 in the disconnected state is determined based on the comparison of the previous wireless communications parameters and the current wireless communication parameters. In one embodiment, the approximate location is determined by using a classification algorithm. In one embodiment, the approximate location is determined using a Kullback-Leibler (KL) divergence. In one embodiment, the approximate location is determined using a Jensen Shannon (JS) divergence.

In one embodiment, the approximate location of the hospital bed 100 may be output to a display interface, such as display interface of the central computer 470.

It will be appreciated that the method 1200 may be used to determine the approximate location of a patient support apparatus such as the hospital bed 100 associated with the hospital bed communication device 200 when the hospital bed communication device 100 has been previously connected to the wireless node 400, 550 or the central computer 470 via the one or more communications interfaces 230.

It should be expressly understood that not all technical effects mentioned herein need to be enjoyed in each and every embodiment of the present technology. For example, embodiments of the present technology may be implemented without the user enjoying some of these technical effects, while other non-limiting embodiments may be implemented with the user enjoying other technical effects or none at all.

Some of these steps and signal sending-receiving are well known in the art and, as such, have been omitted in certain portions of this description for the sake of simplicity. The signals can be sent-received using optical means (such as a fiber-optic connection), electronic means (such as using a wired or wireless connection), and mechanical means (such as pressure-based, temperature based or any other suitable physical parameter based).

Modifications and improvements to the above-described implementations of the present technology may become apparent to those skilled in the art. The foregoing description is intended to be exemplary rather than limiting. The scope of the present technology is therefore intended to be limited solely by the scope of the appended claims.

The invention claimed is:

1. A method of connecting a patient support apparatus to a communication network, the patient support apparatus comprising: a base, a patient support assembly mounted to the base, a patient support communication device comprising: a processor, a first wireless communication interface operatively connected to the processor and being configured to be activated to transmit and receive a first type of wireless signal, and a second wireless communication interface operatively connected to the processor and being configured to be activated to transmit a second type of wireless signal, the patient support apparatus being electrically connectable to a power source, the method being executed by the processor, the method comprising:
   receiving an electrical connection indication of an electrical connection of the patient support apparatus to a wireless node to receive electrical power therefrom, the wireless node being electrically connected to a facility power source, the wireless node being connected to the communication network;
   in response to the receiving the electrical connection indication of the electrical connection of the patient support apparatus to the wireless node:
   causing activation of the first wireless communication interface;
   receiving, from the wireless node, a first wireless signal, the first wireless signal being of the first type of wireless signal;
   in response to the receiving the first wireless signal:
   causing transmission of a second wireless signal of the first type, the transmitting thereby connecting the patient support apparatus to the wireless node;
   receiving an electrical disconnection indication of the patient support apparatus being electrically disconnected from the wireless node; and
   in response to the receiving the electrical disconnection indication of the electrical disconnection:
   causing activation of the second wireless communication interface.

2. The method of claim 1, wherein the electrical connection is a wired electrical connection.

3. The method of claim 1, wherein the processor is connected to a control unit of the patient support apparatus to receive the electrical connection indication of the electrical connection and the electrical disconnection indication of the electrical disconnection of the patient support apparatus.

4. The method of claim 1, wherein the causing activation of the second communication interface comprises causing activation of the second communication interface in a discovery mode.

5. The method of claim 2, wherein the receiving the electrical connection indication of the electrical connection of the patient support apparatus comprises receiving a unique password indication of a unique password transmitted by the wireless node via the wired electrical connection;

and wherein the second wireless signal of the first type comprises the unique password indication of the unique password.

6. The method of claim 1, wherein the causing the transmission of the second wireless signal comprises causing transmission of a unique identifier indication of a unique identifier of the patient support apparatus.

7. The method of claim 1, wherein the causing the activation of the second communication interface comprises causing transmission of a third wireless signal of the second type, the third wireless signal including a unique patient device identifier indication of a unique identifier of the patient support communication device.

8. The method of claim 1, wherein the second type of wireless signal has a shorter range than the first type of wireless signal.

9. The method of claim 1, wherein the connecting the patient support apparatus to the wireless node is performed using a Wi-Fi Protected Setup (WPS).

10. The method of claim 1, wherein the second communication interface comprises at least one of: a Bluetooth communication interface, and an ultra-wideband (UWB) communication interface.

11. A patient support apparatus comprising: a base; a patient support assembly connected to the base; a patient support apparatus communication device mounted to one of the base and the patient support assembly, the patient support apparatus communication device comprising:
a processor,
a first wireless communication interface operatively connected to the processor and being configured to be activated to transmit and receive a first type of wireless signal, and
a second wireless communication interface operatively connected to the processor and being configured to be activated to transmit a second type of wireless signal,
the patient support communication device being configured to:
in response to the receiving an electrical connection indication that the patient support apparatus is electrically connected to a wireless node, the wireless node being electrically connected to a facility power source:
causing activation of the first wireless communication interface to connect the patient support apparatus communication device to the wireless node via the first type of wireless signal; and
in response to the receiving an electrical disconnection indication that the patient support apparatus is electrically disconnected from wireless node:
causing activation of the second communication interface to transmit the second type of wireless signal.

12. The patient support apparatus of claim 11, wherein the causing the activation of the second communication interface comprises causing activation of the second communication interface into a discovery mode.

13. The patient support apparatus of claim 11, wherein the second type of wireless signal has a shorter range than the first type of wireless signal.

14. The patient support apparatus of claim 11, wherein the patient support communication device is associated with a patient support apparatus identifier;
and wherein the patient support communication device is configured to transmit a patient support apparatus identifier indication of the patient support apparatus identifier.

15. A method for determining an approximate location of at least one patient support apparatus in a facility, the at least one patient support apparatus comprising a patient support apparatus communication device comprising at least one communication interface for transmitting a first type of wireless signal and a second type of wireless signal and having been connected to a given one of a plurality of wireless nodes in the facility, the method being executed by a processor connected to at least one of the plurality of wireless nodes over a communication network, the method comprising:
receiving, by the processor, previous wireless communication parameters associated with the at least one patient support apparatus, the previous wireless communication parameters having been determined by the given one of the plurality of wireless nodes by previously receiving the first type of wireless signal from the patient support apparatus communication device of the at least one patient support apparatus;
receiving, by the processor, current wireless communication parameters associated with the patient support apparatus communication device of the at least one patient support apparatus, the current wireless communication parameters having been determined by at least a portion of the plurality of wireless nodes by receiving the second type of wireless signal from the patient support apparatus communication device;
comparing, by the processor, the previous wireless communication parameters and the current wireless communication parameters; and
determining, by the processor, the approximate location of the at least one patient support apparatus based on the comparison of the previous wireless communication parameters and the current wireless communication parameters.

16. The method of claim 15, wherein the at least one patient support apparatus has been previously electrically connected to the given one of the wireless node via an electrical wire to receive electrical power therefrom.

17. The method of claim 15, wherein the at least one patient support apparatus has been previously connected to the given one of the wireless node via a wireless communication link.

18. The method of claim 15, wherein the previous wireless communication parameters comprise: a unique identifier of at the least one patient support apparatus, and a previous inquiry response rate (IRR) of at the least one patient support apparatus.

19. The method of claim 15, wherein the processor comprises a processor of one of wireless nodes of the plurality of wireless nodes.

20. The method of claim 15, wherein the processor comprises a processor of the given wireless node.

21. The method of claim 15, wherein the current wireless communication parameters are indicative of a current spatial density of patient support apparatuses in the facility.

22. The method of claim 15, wherein the current wireless communication parameters are indicative of a past spatial density of patient support apparatuses in the facility.

23. The method of claim 15, wherein the current wireless communication parameters comprise a current inquiry response rate (IRR) of the at least one patient support apparatus.

24. The method of claim 15, wherein the previous wireless communication parameters comprises a previous IRR of at least one patient support apparatus.

25. The method of claim 15, wherein the determining the approximate location is performed by using a classification algorithm.

26. The method of claim 15, wherein the determining the approximate location is performed by using a Kullback-Leibler (KL) divergence.

27. The method of claim 15, wherein determining the approximate location is performed by using a Jensen Shannon (JS) divergence.

* * * * *